US010820839B2

(12) United States Patent  
Sturgeon et al.

(10) Patent No.: US 10,820,839 B2  
(45) Date of Patent: Nov. 3, 2020

(54) ELECTRONIC TABLET FOR USE IN MRI

(71) Applicant: Indiana University Research and Technology Corporation, Indianapolis, IN (US)

(72) Inventors: Jeffrey Sturgeon, Bloomington, IN (US); Alexander Shroyer, Bloomington, IN (US); Sophia Angela Vinci-Booher, Bloomington, IN (US); Karin James, Bloomington, IN (US)

(73) Assignee: Indiana University of Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/266,550

(22) Filed: Feb. 4, 2019

(65) Prior Publication Data

US 2019/0231229 A1    Aug. 1, 2019

Related U.S. Application Data

(63) Continuation-in-part of application No. PCT/US2017/045237, filed on Aug. 3, 2017.

(Continued)

(51) Int. Cl.
*A61B 5/11* (2006.01)  
*G01R 33/28* (2006.01)  
(Continued)

(52) U.S. Cl.
CPC ............ *A61B 5/1124* (2013.01); *A61B 5/055* (2013.01); *A61B 5/748* (2013.01); *G01R 33/283* (2013.01); *G01R 33/4806* (2013.01); *G06F 3/041* (2013.01)

(58) Field of Classification Search
CPC ... A61B 5/055; G01R 33/283; G01R 33/4806  
See application file for complete search history.

(56) References Cited

U.S. PATENT DOCUMENTS 4,702,538 A    10/1987 Hutter  
5,393,928 A    2/1995 Cribb et al.  
(Continued)

FOREIGN PATENT DOCUMENTS

WO    2015087243 A1    6/2015

OTHER PUBLICATIONS

International Preliminary Report on Patentability issued by the International Searching Authority, dated Feb. 5, 2019, for International Patent Application No. PCT/US2017/045237; 8 pages.

(Continued)

*Primary Examiner* — Gregory H Curran  
(74) *Attorney, Agent, or Firm* — Faegre Drinker Biddgle & Reath LLP

(57) ABSTRACT

A system for recording visually guided motor activity within a bore of an MRI machine, comprising a tablet configured for mounting within the bore of the MRI machine, the tablet comprising a shielded housing, a touchscreen display mounted within the housing, and a receiver board, an interface box coupled to a controller configured to control operation of the touchscreen display, the interface box being located remotely from the bore and comprising a transmitter board for processing signals from the controller and transmitting processed signals to the receiver board of the tablet, and a cable connected between the tablet and the interface box, the cable comprising a plurality of conductors to carry signals between the receiver board and the transmitter board.

32 Claims, 31 Drawing Sheets

Related U.S. Application Data

(60) Provisional application No. 62/370,372, filed on Aug. 3, 2016.

(51) Int. Cl.
*G01R 33/48* (2006.01)
*A61B 5/055* (2006.01)
*A61B 5/00* (2006.01)
*G06F 3/041* (2006.01)

(56) References Cited

U.S. PATENT DOCUMENTS

| | | |
|---|---|---|
| 8,073,526 B2 | 12/2011 | Graham et al. |
| 9,379,759 B2 | 6/2016 | Platt |
| 2002/0056187 A1* | 5/2002 | Doi ............... G01R 33/383 29/607 |
| 2006/0038730 A1* | 2/2006 | Parsche ............. H01Q 7/04 343/741 |
| 2013/0088233 A1 | 4/2013 | Martius et al. |
| 2014/0262933 A1 | 9/2014 | Lockwood |
| 2016/0015352 A1 | 1/2016 | Brown et al. |
| 2016/0212893 A1* | 7/2016 | Byler ............... H04B 1/38 |
| 2016/0228005 A1* | 8/2016 | Bammer ............ A61B 5/055 |

OTHER PUBLICATIONS

International Search Report and Written Opinion issued by the ISA/US Commissioner for Patents, dated Dec. 4, 2017, for International Application No. PCT/US2017/045237; 11 pages.

\* cited by examiner

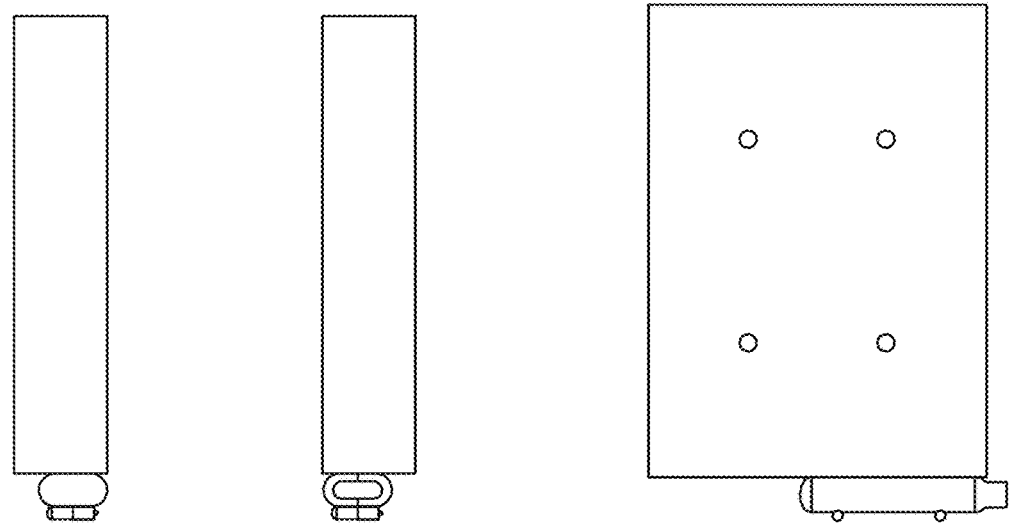
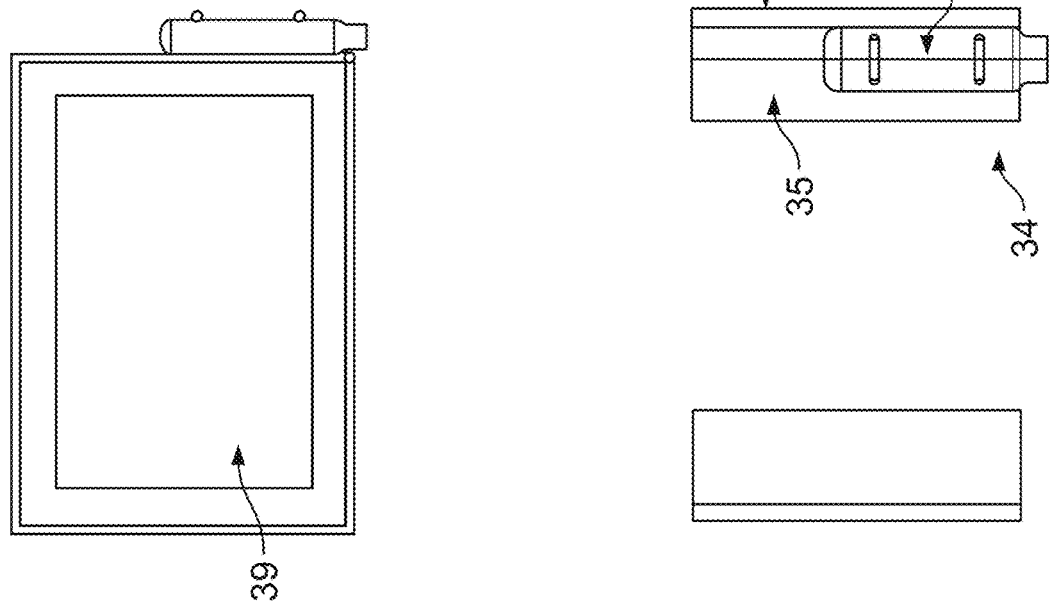
FIG. 5

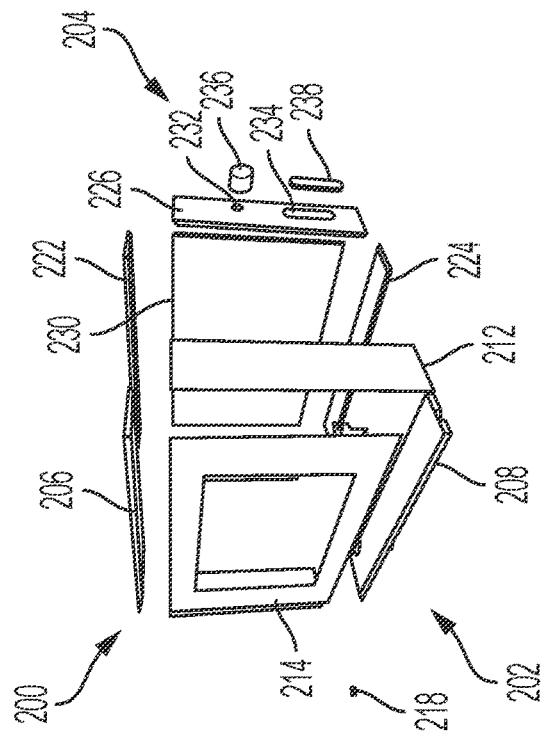
FIG. 27
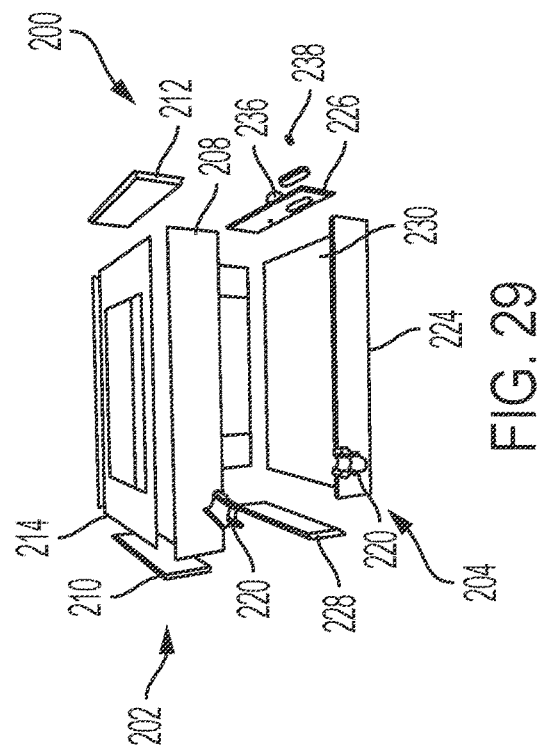
FIG. 29
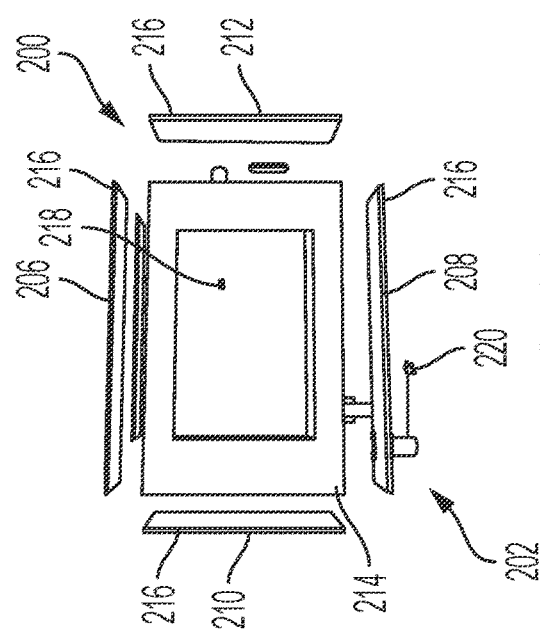
FIG. 26
FIG. 28

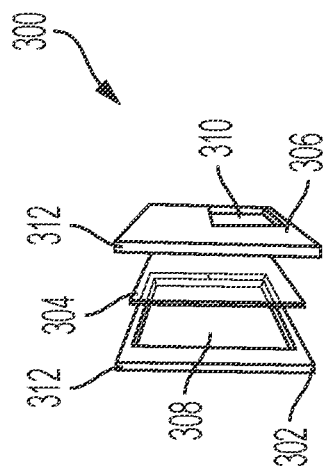
FIG. 31
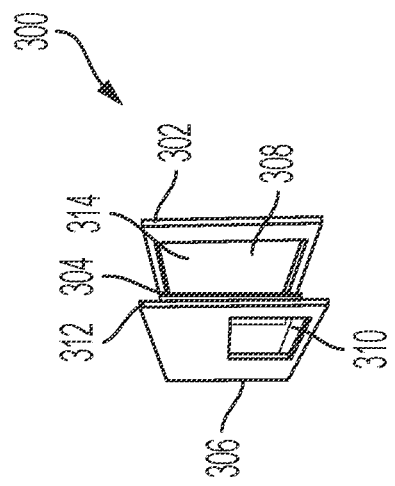
FIG. 33
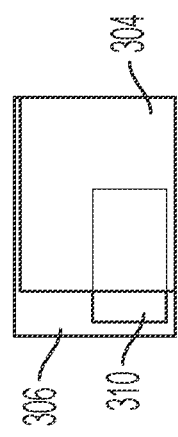
FIG. 30
FIG. 32

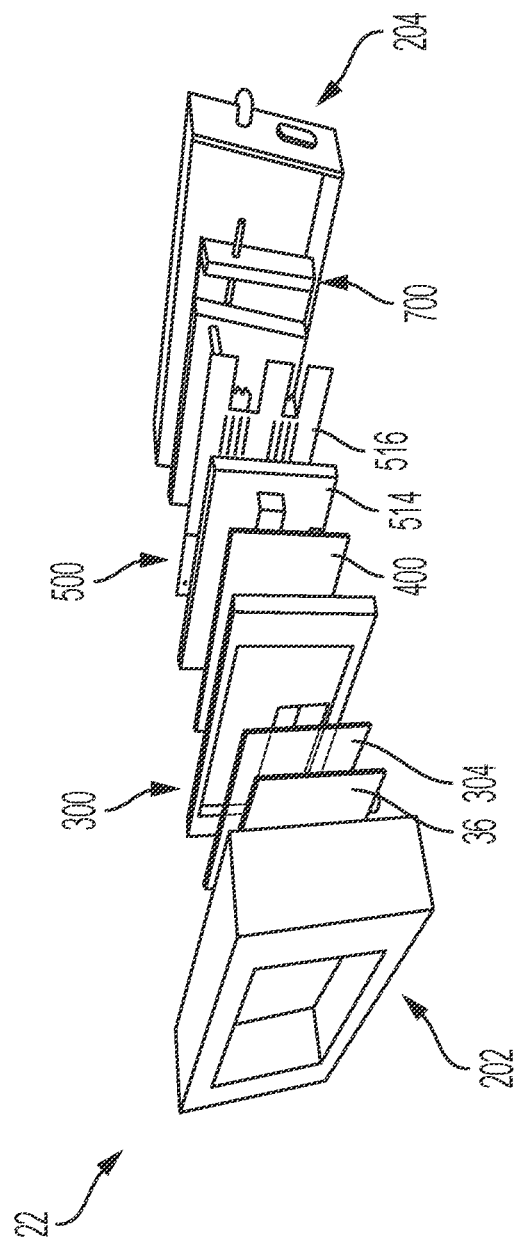
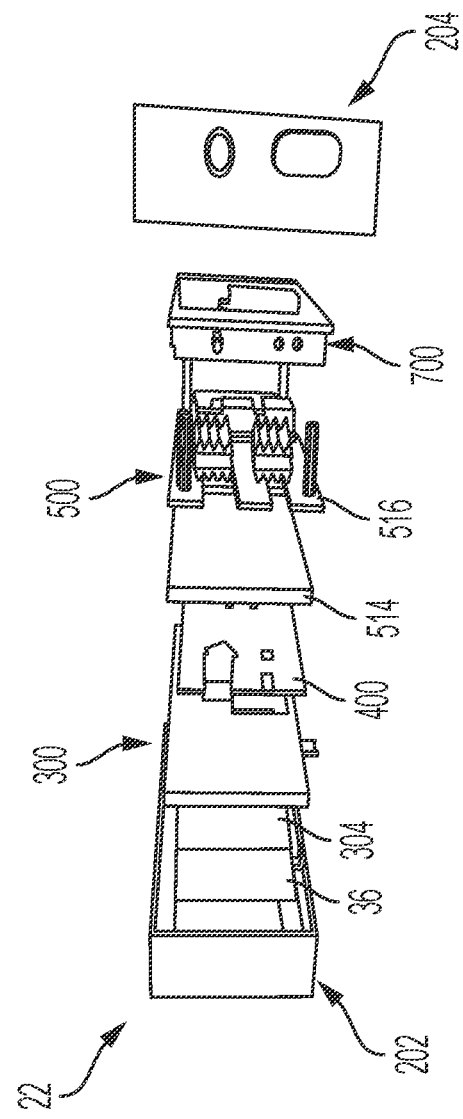

ELECTRONIC TABLET FOR USE IN MRI

PRIORITY CLAIM

This application is a continuation-in-part application filing under 35 U.S.C. § 111(a) of International Application No. PCT/US2017/45237, titled "ELECTRONIC TABLET FOR USE IN FUNCTIONAL MRI," filed on Aug. 3, 2017, which claims priority to U.S. Provisional Application No. 62/370,372, which is entitled "ELECTRONIC TABLET FOR USE IN FUNCTIONAL MRI," and was filed on Aug. 3, 2016, the entire disclosures of which are expressly incorporated herein by reference in its entirety.

TECHNICAL FIELD

The present invention relates generally to touch interface devices and more particularly to a tablet-sized real-time video display with touch interface that can function in the bore of a Magnetic Resonance Imaging ("MRI") machine.

BACKGROUND

The relationships between visually guided motor actions (such as hand writing) and the accompanying brain activity may provide insight into psychological processes such as high-level cognition. For example, by better understanding the brain activity that occurs as a person exercises the motor skills necessary to perform handwriting with visual feedback (i.e., the person looks at the hand performing the hand writing), researchers may learn more about how people learn to write. Indeed, brain images obtained during visually guided motor activity may lead to more effective rehabilitation programs for neurologically impaired individuals (e.g., stroke survivors) and/or educational programs for language comprehension, visual thinking and mathematics, etc. All of this requires the capture of brain images of a subject at the same time the subject's performance of the visually guided motor activity is being recorded. In the handwriting context, brain scans must be obtained as the subject's visually guided handwriting is being recorded to correlate the scans with motor actions that generate the handwriting.

The primary means of brain imaging today is MRI scanning. The MRI machines produce extremely intense magnetic fields which render inoperable virtually all electronic devices in the vicinity of the bore of the scanner. Accordingly, earlier research into the interrelationships between neurological activity and motor actions omitted visual feedback. In the handwriting context, subjects were placed in an MRI machine and scanned while they wrote onto a paper tablet or onto a transparent touchscreen that had no display capabilities. Although the subjects were being scanned as their handwriting was being simultaneously recorded, the handwriting was not visually guided (i.e., they could not watch their hand writing or they could watch only what they wrote (without their hand) with the assistance of mirrors). Thus, the significance of visual feedback during handwriting could not be adequately studied.

As such, there exists a need for a touchscreen device with real-time display capable of functioning in the strong electromagnetic field of an MRI machine to enable researchers to simultaneously capture both visually guided hand actions and brain imaging data.

SUMMARY

According to one embodiment of the present disclosure, a system for recording visually guided motor activity within a bore of an MRI machine is provided, comprising: a tablet configured for mounting within the bore of the MRI machine, the tablet comprising a housing having a first opening, a touchscreen display mounted within the housing for access through the first opening, a first shielding layer disposed over the touchscreen display and spanning the first opening, a second shielding layer disposed between the first shielding layer and the touchscreen display and spanning the first opening, and a receiver board, the housing being formed of an encasement material that reduces RF interference with the touchscreen/display and the receiver board; an interface box coupled to a controller configured to control operation of the touchscreen display, the interface box being located remotely from the bore and comprising a transmitter board for processing signals from the controller and transmitting processed signals to the receiver board of the tablet; and a cable connected between the tablet and the interface box, the cable comprising a plurality of conductors to carrying signals between the receiver board and the transmitter board. In one aspect of this embodiment, the encasement material of the housing is FR-4 composite material with copper cladding on both sides. In another aspect, the housing includes a 3D printed bottom plate and a 3D printed top plate that includes the first opening. In still another aspect, the first shielding layer is formed from silver plastic mylar material. In a variant of this aspect, the second shielding layer is formed from copper mesh material. In another aspect of this embodiment, the touchscreen display is a touch-sensitive LCD display. In another aspect, the housing comprising a back wall, a forward wall, a pair of side walls, an upper wall and a lower wall, the walls being electrically joined together on interior and exterior sides using soldered copper tape. In a variant of this aspect, the forward wall includes the first opening and one of the side walls includes a second opening for receiving the cable. In a further variant of this aspect, the interior side of each wall is beveled at an intersection with an adjacent wall. In yet another aspect of this embodiment, the system further comprises a mounting bracket coupled to the tablet housing and a support configured to mount within the bore and support the mounting bracket. In a variant of this aspect, the support comprises a pair of curved braces coupled to a channel and a pair of lower braces, the channel including a C-shaped opening configured to slidably receive the mounting bracket. In another variant, the support further comprises a tab connected to each lower brace and configured to couple the support to the MRI machine. In still another variant, the mounting bracket comprises an insert sized to fit within the C-shaped opening and a mounting plate attached to a back wall of the tablet housing. In another aspect of this embodiment, the cable comprises a plurality of Ethernet cable sections. In another aspect, a shielding braid surrounding the conductors is formed from copper. In yet another aspect, the cable further comprises an outer nylon jacket braid surrounding a shielding braid surrounding the conductors. In still another aspect, the receiver board and the transmitter board each include a plurality of buffers.

In another embodiment of the present disclosure, a tablet assembly for recording visually guided motor activity within a bore of an MRI machine is provided, comprising: a tablet configured for mounting within the bore of the MRI machine, the tablet comprising a housing having a first opening, a touchscreen display mounted within the housing for access through the first opening, at least one shielding layer disposed over the touchscreen display and spanning the first opening, and a receiver board, the housing being formed of an encasement material that reduces RF interference with the touchscreen display and the receiver board; an interface box located remotely from the bore and comprising a transmitter board for transmitting signals to the receiver board of the tablet; and a cable connected between the tablet and the interface box, the cable comprising a plurality of conductors to carrying signals between the receiver board and the transmitter board. In one aspect of this embodiment, the encasement material of the housing is FR-4 composite material with copper cladding on both sides. In another aspect, at least one shielding layer comprises a silver plastic mylar layer and a copper mesh layer. In another aspect, the tablet assembly further comprises a mounting bracket coupled to the tablet housing and configured to couple to a support mounted within the bore. In still another aspect of this embodiment, the cable comprises a plurality of Ethernet cable sections and a nylon jacket braid surrounding a shielding braid surrounding the conductors.

According to a further embodiment of the present disclosure, a method of studying brain activity associated with visually guided motor activity is provided, comprising: locating a patient in a bore of an MRI machine; locating a tablet in the bore, the tablet comprising a touchscreen display within reach and line of sight of the patient; instructing the patient to perform a visually guided motor activity through interaction with the touchscreen display; and simultaneously recording the interaction with the touchscreen display and scanning the brain of the patient with the MRI machine. In one aspect of this embodiment, the method further includes providing entertainment to the patient during the scanning of the brain of the patient with the MRI machine. In another aspect of this embodiment, the method further includes enabling a touch-based interaction for the entertainment within the bore of the MRI machine.

In yet another embodiment of the present disclosure, a tablet is provided for an Magnetic Resonance Imaging (MRI) machine. The tablet comprises a housing having a front housing assembly and a rear housing assembly, the front housing assembly having a first opening, a touchscreen display mounted within the housing for access through the first opening, at least one shielding layer disposed over the touchscreen display and spanning the first opening, and at least one layer of carbon fiber formed on an outer surface of the housing as an encasement material that reduces RF interference with the touchscreen display. The at least one layer of carbon fiber prevents an internal electrical signal from interfering with one or more MRI images received from the MRI machine and signals generated from the MRI from interfering with the functioning of the tablet.

In one example, the front housing assembly includes at least one panel, and the rear housing assembly includes at least one panel, each panel having a thickness of at least 2 millimeters. In a variation, the at least one panel of the front housing assembly and the at least one panel of the rear housing assembly are assembled with a conductive epoxy. In another variation, the at least one panel of the front housing assembly and the at least one panel of the rear housing assembly are molded with a carbon fiber fabric.

In another example, the tablet further comprises a display housing assembly including a front housing support, a monitor, and a rear housing support, wherein a strip made of at least one of: copper, carbon, and/or nickel is applied at least partially along an outer edge of at least one of: the front housing support and the rear housing support. In a variation, the front housing support includes an opening for viewing one or more images displayed on the monitor, and the rear housing support includes an opening for providing access to at least one cable connected to the monitor. In another variation, the front housing support includes a shielded window having a copper mesh.

In yet another example, the tablet further comprises an optical driver assembly configured to convert an optical signal received from an interface box coupled to a controller. In a variation, the optical driver assembly includes a USB host port fiber driver connected to a USB optic cable, and a HDMI driver connected to a HDMI optic cable. In another variation, each of the USB host port fiber driver and the HDMI driver is sandwiched between two separate heat sinks.

In still another example, the tablet further comprises an interface box including a cover and a base having a USB optical drive and a HDMI optical drive. In a variation, the cover and the base are made of aluminum. In another variation, the base includes at least one USB port connected to the USB optical drive, and at least one HDMI port connected to the HDMI optical drive.

In yet still another example, the tablet further comprises a shielding jacket configured to encase at least one component of the tablet, wherein the shielding jacket is made of a multi-metallized fabric. In a variation, one or more external seams associated with the shielding jacket are attached together with a polyimide tape.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The above-mentioned and other features of this disclosure and the manner of obtaining them will become more apparent and the disclosure itself will be better understood by reference to the following description of embodiments of the present disclosure taken in conjunction with the accompanying drawings, wherein:

FIG. 5 provides multiple views of a tablet housing according to the present disclosure;

FIGS. 26-29 are exploded views of another tablet housing according to the present disclosure;

FIG. 30 is a front view of a display housing assembly according to the present disclosure;

FIGS. 31 and 33 are perspective views of the display housing assembly of FIG. 30;

FIG. 32 is a rear view of the display housing assembly of FIG. 30;

FIGS. 60-61 are exploded views of an exemplary configuration of another tablet using the tablet housing shown in FIGS. 26-29 according to the present disclosure.

Figure 1:
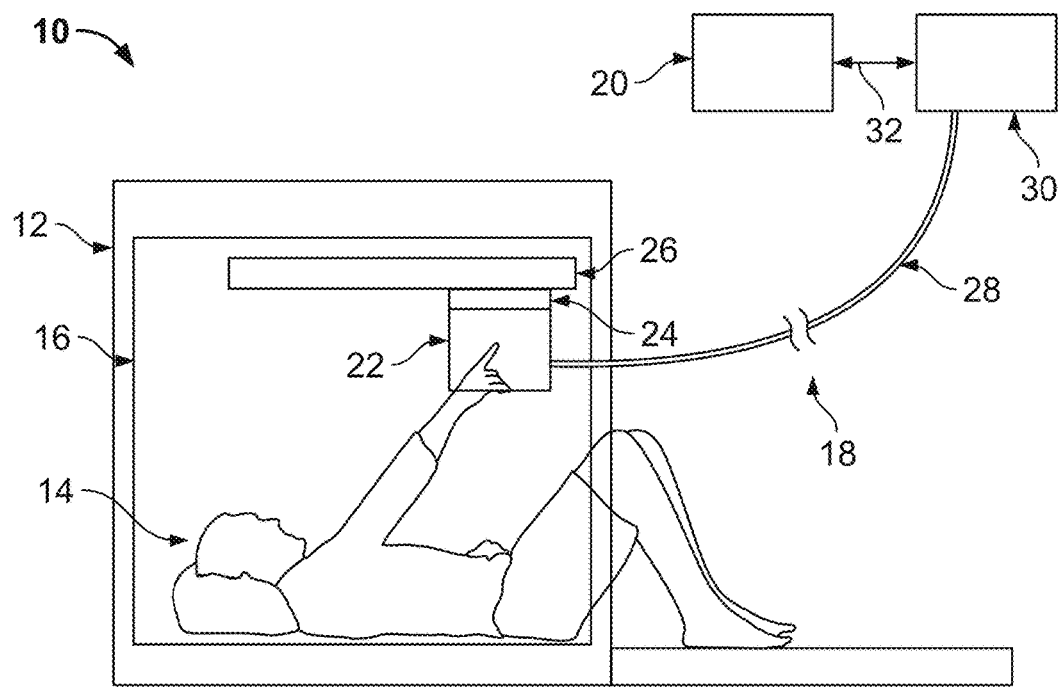
FIG. 1 is a conceptual drawing of a system for simultaneously recording motor activity and scanning brain activity according to one embodiment of the present disclosure.

While the present disclosure is amenable to various modifications and alternative forms, specific embodiments have been shown by way of example in the drawings and are described in detail below. The present disclosure, however, is not to limit the particular embodiments described. On the contrary, the present disclosure is intended to cover all modifications, equivalents, and alternatives falling within the scope of the appended claims.

DETAILED DESCRIPTION

The embodiments disclosed below are not intended to be exhaustive or to limit the disclosure to the precise forms disclosed in the following detailed description. Rather, the embodiments are chosen and described so that others skilled in the art may utilize their teachings.

One of ordinary skill in the art will realize that the embodiments provided can be implemented in hardware, software, firmware, and/or a combination thereof. For example, the controller disclosed herein may form a portion of a processing subsystem including one or more computing devices having memory, processing, and communication hardware. The controller may be a single device or a distributed device, and the functions of the controller may be performed by hardware and/or as computer instructions on a non-transient computer readable storage medium. For example, the computer instructions or programming code in the controller may be implemented in any viable programming language such as C, C++, HTML, XTML, JAVA or any other viable high-level programming language, or a combination of a high-level programming language and a lower level programming language. As is further described herein, the device of the present disclosure may use the interactive features of traditional desktop operating systems (e.g., Windows®, OS X) or interactive touch-enabled operating systems (e.g., Android, iOS).

The aspects of the present disclosure are described herein primarily in the context of understanding the learning processes associated with handwriting. It should be understood, however, that the device and methods disclosed herein may have application to research in a variety of other areas such as stroke patient rehabilitation, prosthetic use and control, the neurological effects of video gaming, and concussion research to name a few. In each of these areas of research, a subject may be asked to perform a visually guided motor activity that is captured electronically within the bore of an MRI machine where the neurological activity of the subject is recorded simultaneously via the MRI's brain imaging functionality. It should also be understood that the disclosed device and methods may be employed to provide entertainment to patients during long MRI scans by enabling stylus or touch-based interaction with a video game within the bore of the magnet. Moreover, the touch and display capabilities of the present disclosure may be used separately or together in the manner that a computer mouse functions when the monitor is disabled or the monitor functions when the mouse is unplugged. For example, an MRI machine may perform several types of imaging (e.g., functional MRI (fMRI), diffusion MRI (dMRI), etc.).

Referring now to FIG. 1, a system 10 according to one embodiment of the present disclosure generally includes an MRI machine 12 for obtaining brain images of a subject 14 situated within the bore 16 of the machine, a tablet assembly 18 and a computer or controller 20. MRI machine 12 may be any of a variety of devices including, but not limited to, a Siemens TIM Trio 3Tesla scanner, which uses magnetic fields to generate scans of structures internal to the subject's 14 body, such as the brain, according to principles that are known in the art. For example, system 10 can be used in other high electromagnetic fields (EMF) environments (e.g., certain construction/testing areas). Such environments also have a need for MR-safe tablets. The magnetic fields are extremely intense within bore 16 of machine 12. As is shown in FIG. 1, subject 14 is normally lying on his or her back while in bore 16.

Tablet assembly 18 generally includes a tablet 22, a mounting bracket 24 connected to tablet 22, a support 26 for supporting mounting bracket 24, and a cable 28 coupled between tablet 22 and an interface box 30. As is further described herein, interface box 30 communicates with controller 20 over communication link 32. As shown in the figure, tablet 22 is supported within bore 16 by mounting bracket 24 and support 26 such that the subject 14 may interact with tablet 22 while watching his or her motor actions thereby providing visual feedback during the motor tasks. Cable 28 connecting tablet 22 and interface box 30 is long enough to permit interface box 30 to be located a distance from bore 16 that prevents unacceptable disturbance of the electronics functions of interface box 30 by the magnetic fields generated within bore 16 by MRI machine 12. Controller 20 is also positioned a safe distance away from bore 16.

As is further described herein, a general concept of the present disclosure is to locate as much of the electronics used to operate tablet 22 a safe distance away from the strong magnetic field of MRI machine 12. Conventional tablets require substantial circuitry to convert the signals sent out by controller 20 (normally over an HDMI, DVI or VGA cable) into actual red, green and blue pixels turning on and off in the right location at the correct time. According to the present disclosure, much of this circuitry is located far from MRI machine 12 in interface box 30, but still functions as desired in part through the use of special cabling and buffering of signals.

Figure 2:
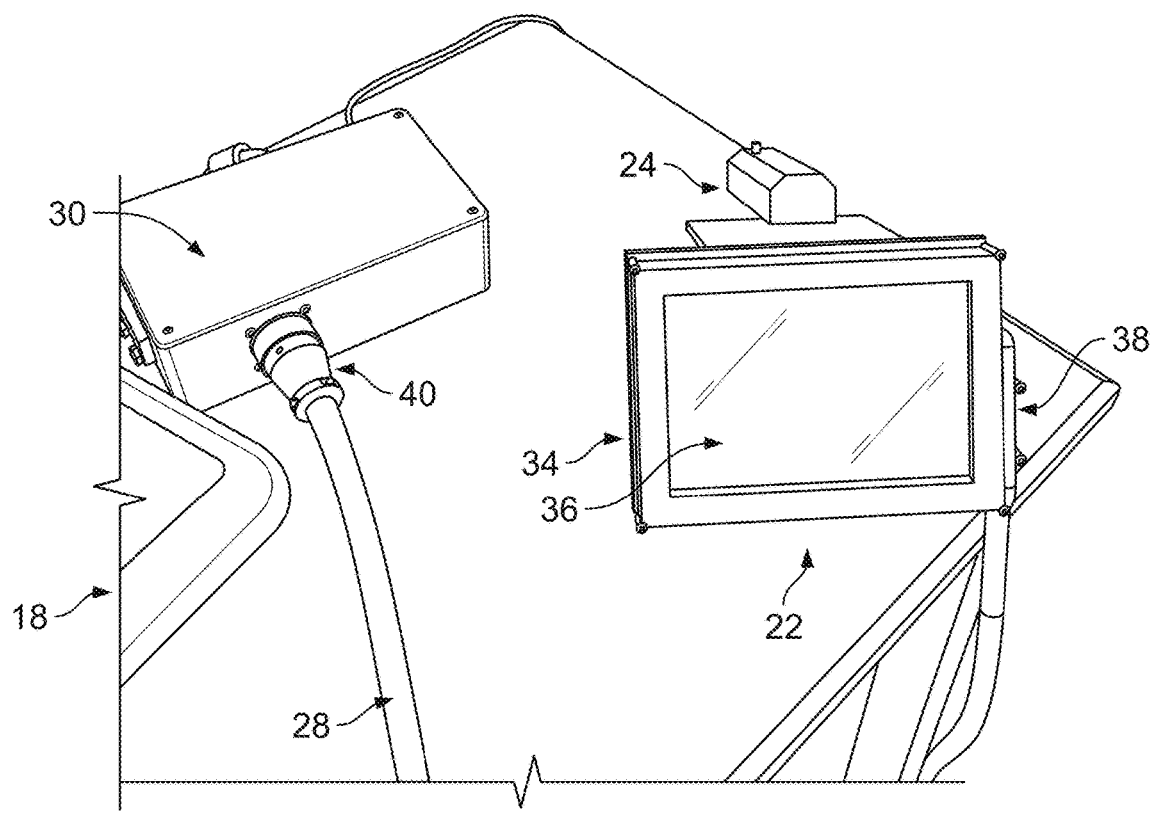
FIG. 2 is a perspective view of a tablet assembly according to one embodiment of the present disclosure.
Figure 3:
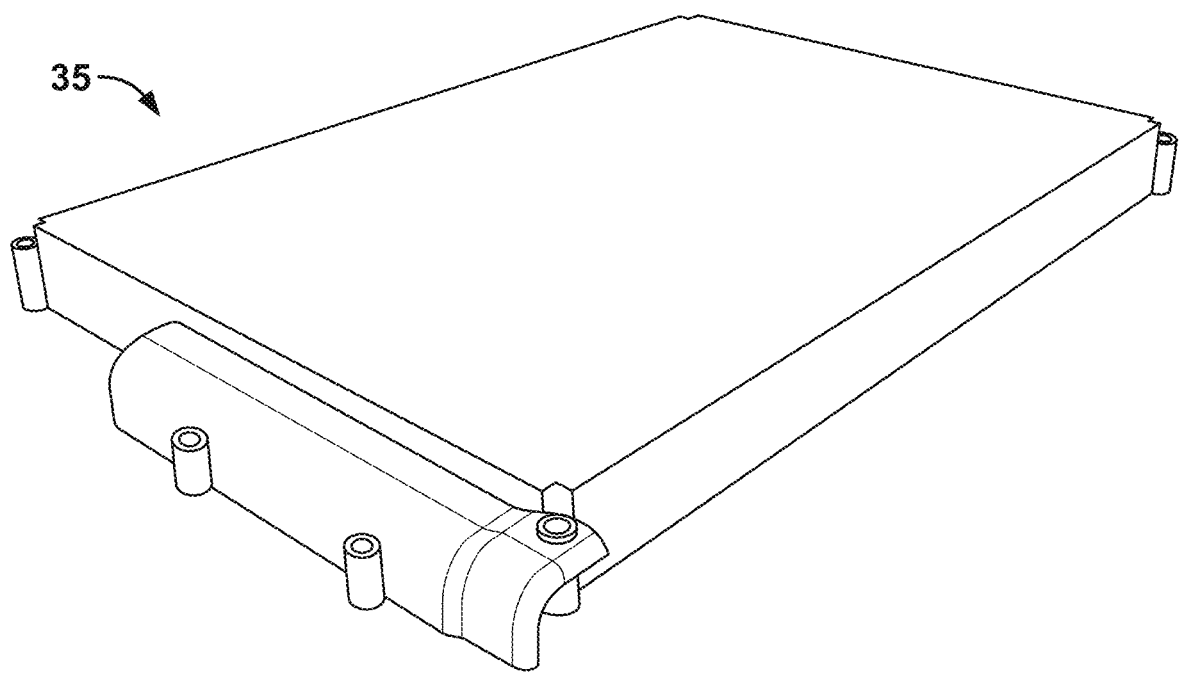
FIG. 3 is a perspective view of a portion of a housing for a touchscreen device with real-time display (hereinafter, a "tablet") according to one embodiment of the present disclosure.
Figure 4:
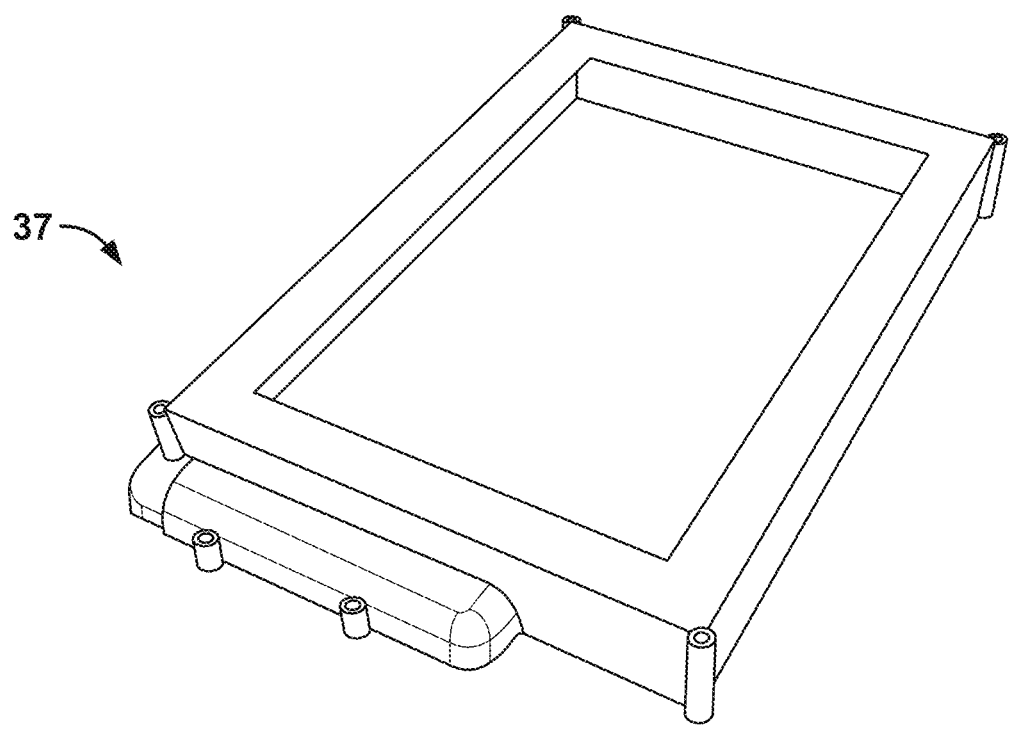
FIG. 4 is a perspective view of another portion of the housing for a tablet.

Referring now to FIG. 2, tablet 22 and interface box 30 are shown connected by cable 28. Tablet 22 generally includes a housing 34, a touchscreen/display 36, and a stress-relief 38 configured to retain cable 28. Mounting bracket 24 is shown mounted to housing 34. Cable 28 is shown connected to interface box 30 using a connector 40. As is further described below, housing 34 may be formed of an encasement material that reduces possible RF interference such as FR-4 composite material (i.e., circuit board material) with ½ ounce copper-clad on both sides. Different encasement materials for housing 34, touchscreen display 36 and cable 28 to reduce possible RF and magnetic interference may include carbon fiber, carbon sheets, carbon granules, stainless steel, bronze and magnesium. FIGS. 3-5 show another embodiment of housing 34 which includes a 3D printed bottom plate 35 and a 3D printed top plate 37 that mates with bottom plate 35 which together form stress-relief 38 and provide an opening 39 for touchscreen display 36.

Figure 6:
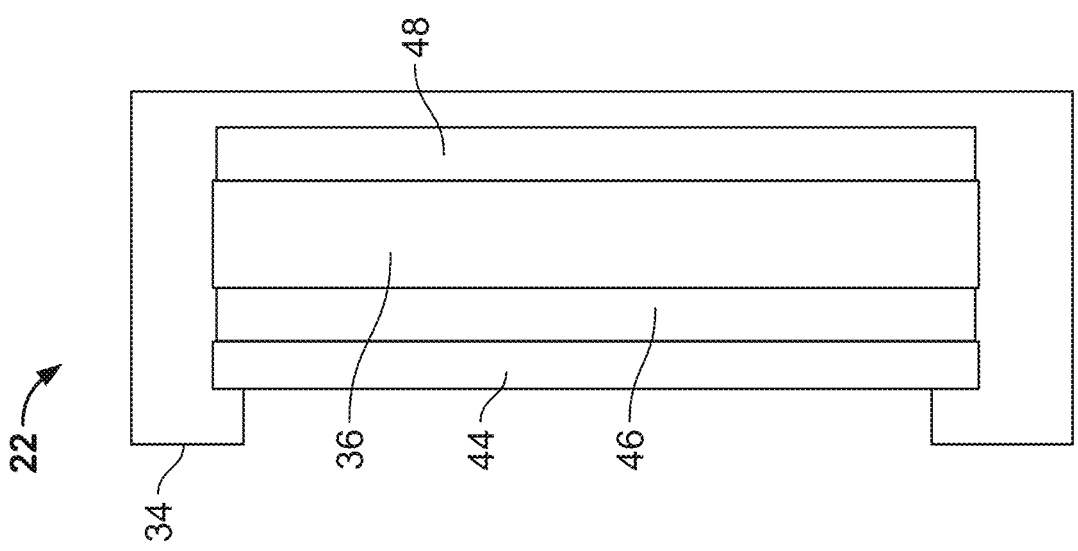

Referring now to FIG. 6, tablet 22 is conceptually depicted as including a touchscreen display 36, a first shielding layer 44, a second shielding layer 46 and a receiver board 48 encased within housing 34. The materials and connections of first shielding layer 44, second shielding layer 46 and housing 34 are selected to prevent interference by (and to) the MRI machine 12 with the electrical operation of touchscreen display 36 and receiver board 48 as is further described below. In one embodiment, first shielding layer 44 is formed from an RF blocking silver plastic mylar material such as SaniSilver™ made by Less EMF, Inc. In one embodiment, second shielding layer 46 is formed from a very fine copper mesh such as VeilShield™ made by Less EMF, Inc. In other embodiments, an RF resistant glass with a copper coating on the inside may be used in place of first shielding layer 44 and second shielding layer 46. While in certain embodiments touchscreen display 36 is described as a touch-sensitive LCD display, in other embodiments an LED or other display may be used.

Figure 7:
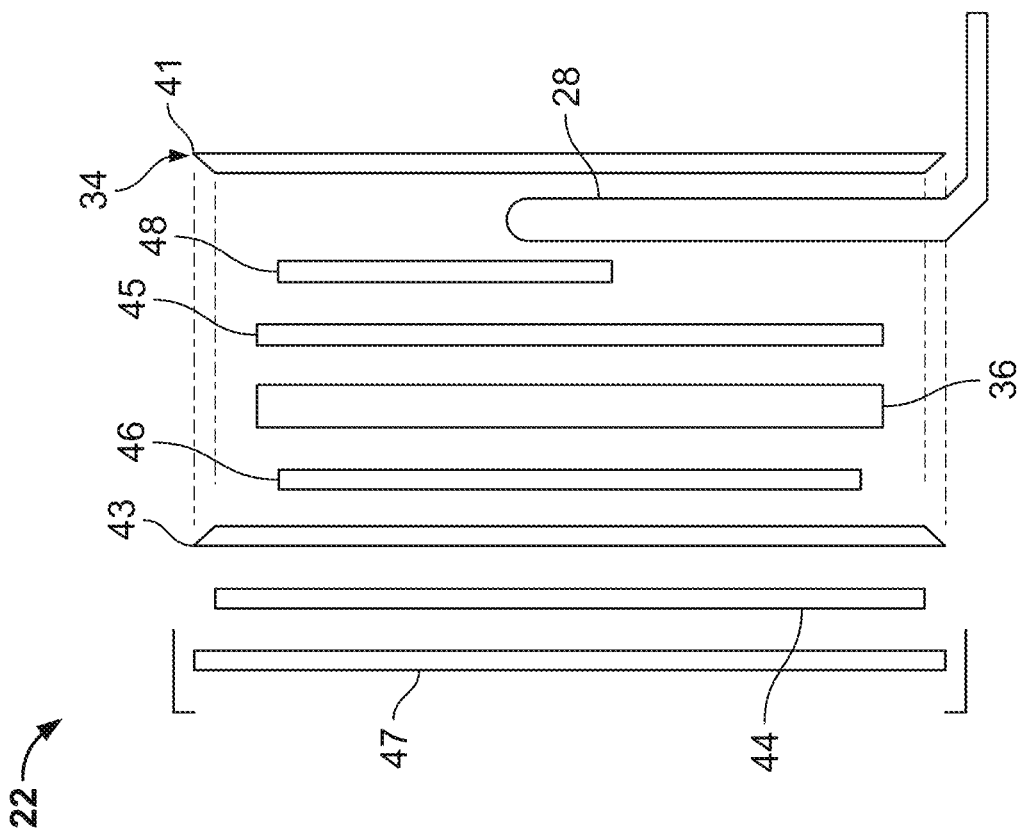
FIGS. 6 and 7 are side, cross-sectional views of the tablet of FIG. 2.

FIG. 7 depicts further details of tablet 22. Housing 34 is shown including a back wall 41, a forward wall 43 and upper and lower walls (shown in dashed lines). Cable 28 extends from within housing 34 (i.e., from receiver board 48) to interface box 30. Touchscreen display 36 is shown mounted within housing 34 backed by an RF absorbent paper 45 and receiver board 48. Second shielding layer 46 including fine micro copper netting is disposed in front of touchscreen display 36. First shielding layer 44 including silver mylar is mounted to forward wall 43 of housing 34. Finally, a touchscreen 47 is mounted to first shielding layer 44.

Referring now to FIGS. 8-11, one embodiment of housing 34 is shown. In this embodiment, housing 34 is made from FR-4 composite material (0.1524 cm thick) such as that of a double sided PC board. Housing 34 generally includes back wall 41, forward wall 43 (as discussed above), side walls 51, 53, upper wall 55 and lower wall 57. In this embodiment, walls 41, 43, 51, 53, 55, 57 are electrically joined together on their interior and exterior sides using soldered copper tape and other materials as described below. Forward wall 43 includes opening 39. Side wall 51 includes an opening 59 for cable 28. In one embodiment, housing 34 is 17.145×12.065×3.175 cm in size and includes the six components listed above. The inside face of each wall is beveled 61 at a 45 degree angle to reduce gaps that could permit passage of RF noise. In the depicted embodiment, opening 39 is 14.24×10.16 cm.

Figure 9:
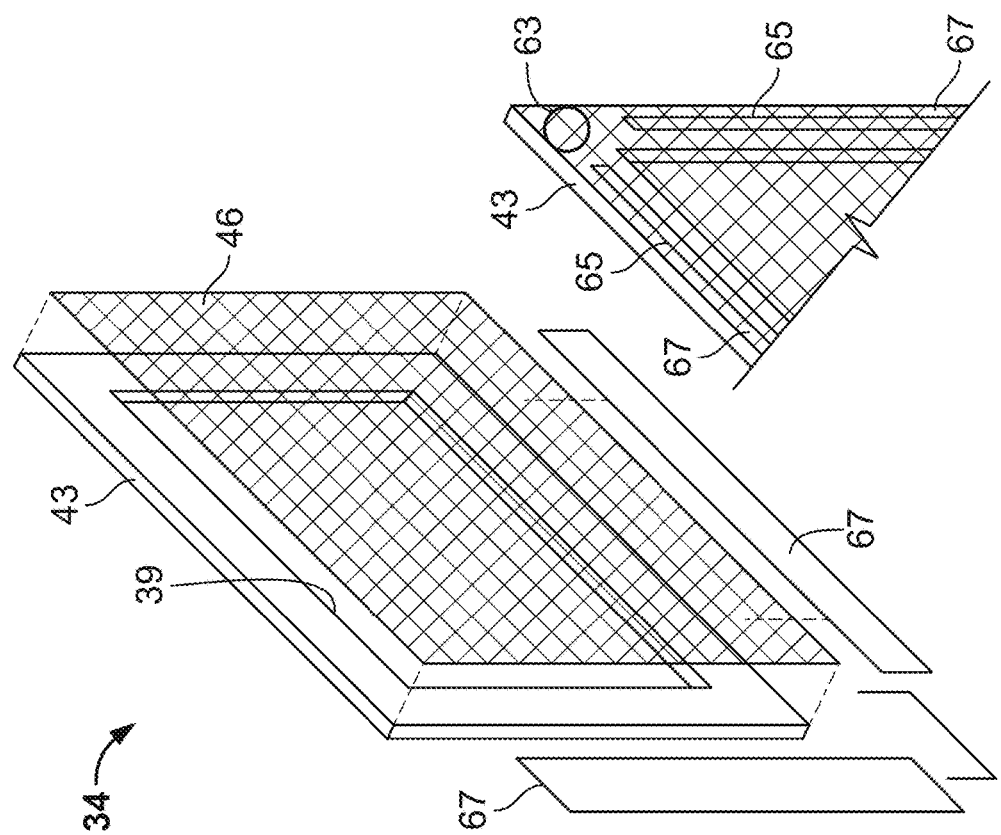
FIG. 9 is a perspective view of a portion of the tablet housing depicted in FIG. 8.
Figure 8:
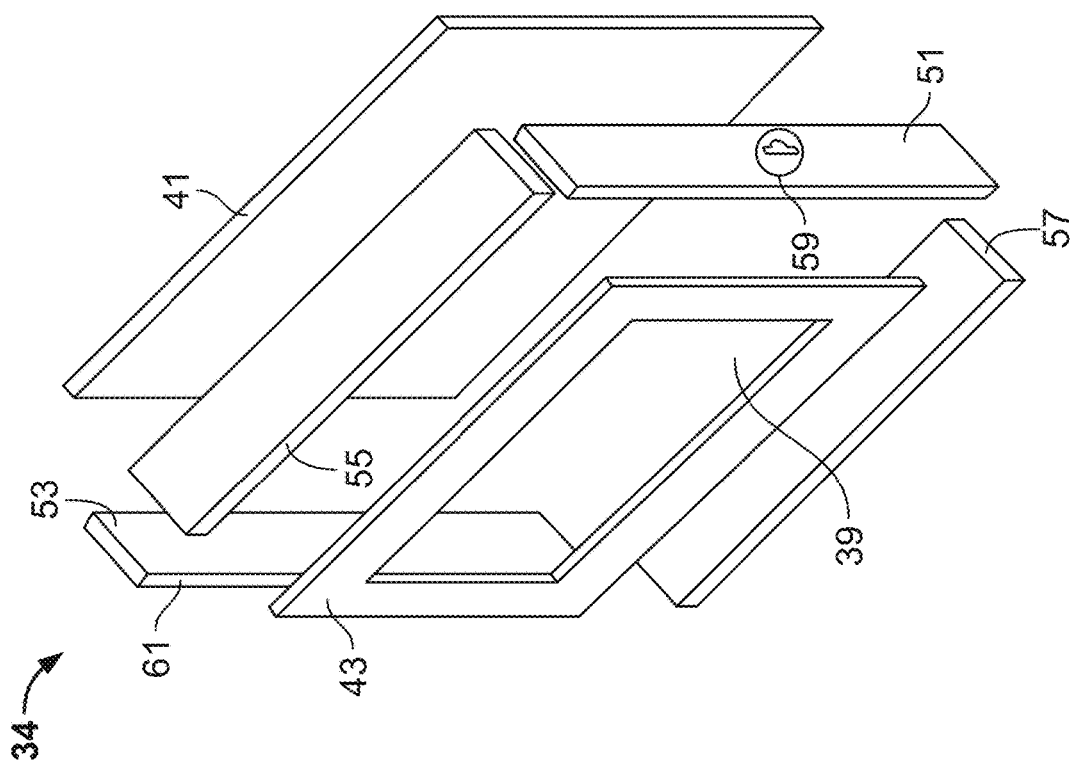
FIG. 8 is an exploded, perspective view of a tablet housing according to the present disclosure.

As best shown in FIG. 9, second shielding layer 46 is positioned across opening 39 on the inside face of forward wall 43. The fine copper net of layer 46 is fine enough to see through but still effective in blocking RF signals generated by the MRI machine 12. Layer 46 is attached to forward wall 43 using silver solder 63 and conductive glue/paint 65. A polyimide tape barrier 67 is placed over the edges of layer 46 around its perimeter. Barrier 67 is an insulator and prevents the electrical ground of tablet 22 from contacting touchscreen display 36 and protects touchscreen display 36 from heat generated by potential current loops.

Figure 10:
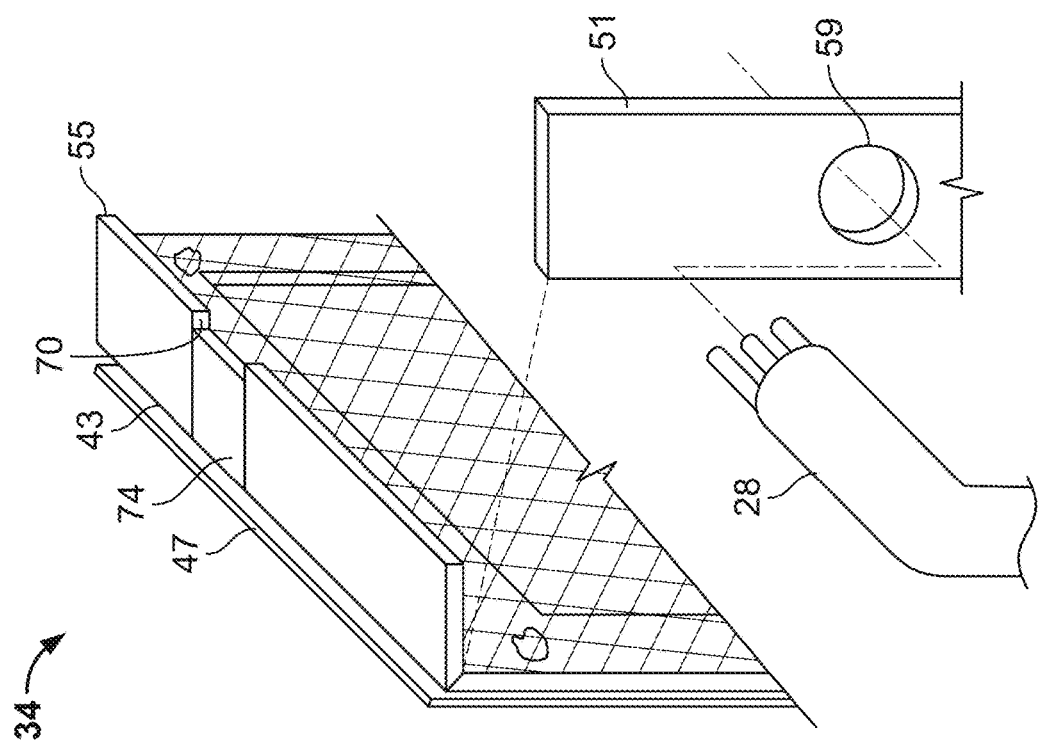
FIG. 10 is a perspective view of another portion of the tablet housing depicted in FIG. 8.

Referring now to FIG. 10, opening 59 is shown in side wall 51 and in one embodiment has a diameter of 1.5875 cm for receiving cable 28. All four walls 51, 53, 55, 57 are soldered to the inside of forward wall 43, ensuring that the copper on the inside of the walls does not contact the copper on the outside of the walls. Conductive glue 65 is then used to seal off any inside seams. A notch 70 is formed into upper wall 55 (approximately 0.9525×0.9525 cm) to receive the cable 72 (FIG. 11) of touchscreen 47. Copper tape is installed along the outside edges of housing 34 and soldered into place. A piece of RF absorbent material 74 is placed on upper wall 55 from forward wall 43 to notch 70. When tablet 22 is fully assembled, another piece of RF material 76 (FIG. 11) is placed on top of cable 72 of touchscreen 47.

Figure 11:
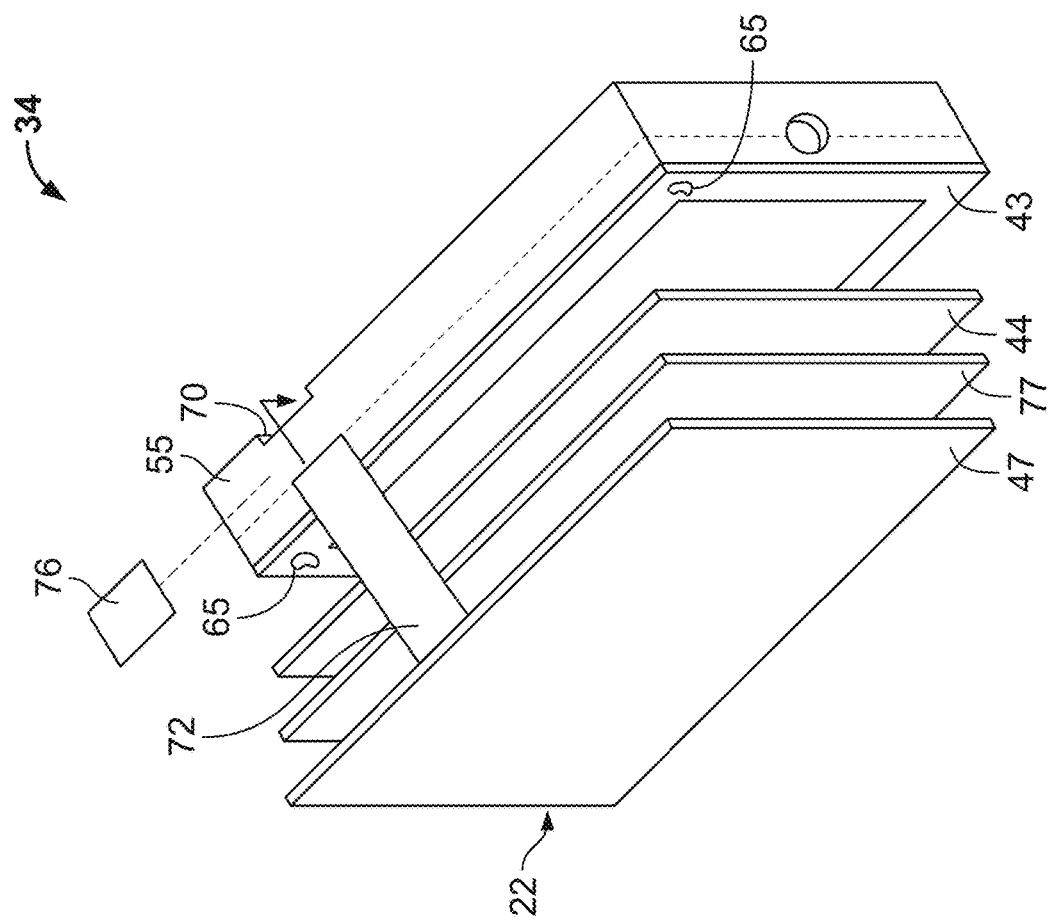
FIG. 11 is an exploded, perspective view of a tablet according to the present disclosure.

Referring now to FIG. 11, first shielding layer 44 of silvered mylar (a section approximately 17.145×12.065 cm) is placed across forward wall 43. The conductive side of layer 44 is positioned to make contact with the copper face of forward wall 43. Conductive glue 65 is placed at each of the four corners of forward wall 43. Next, a faceplate 77 (a super clear polycarbonate panel of approximately 0.15875× 17.145×12.065 in dimension) is placed on top of layer 44. Faceplate 77 inhibits flexing of touchscreen 47 and provides improved tracking. Faceplate 77 is connected to layer 44 using polyimide tapes around its outside edges. Finally, touchscreen 47 is installed and connected.

Figure 12:
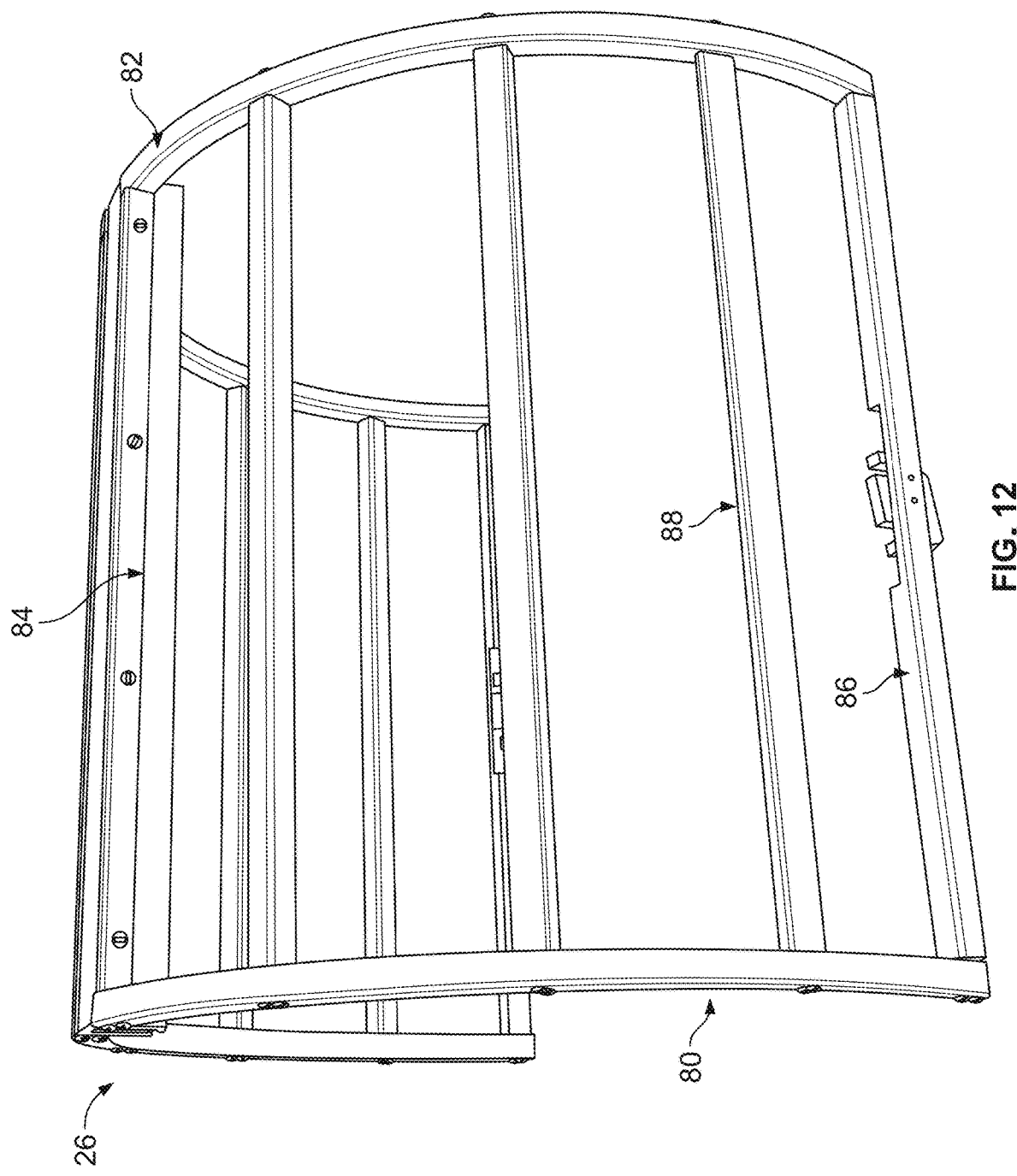
FIGS. 12 and 13 are perspective views of a support according to the present disclosure.
Figure 13:
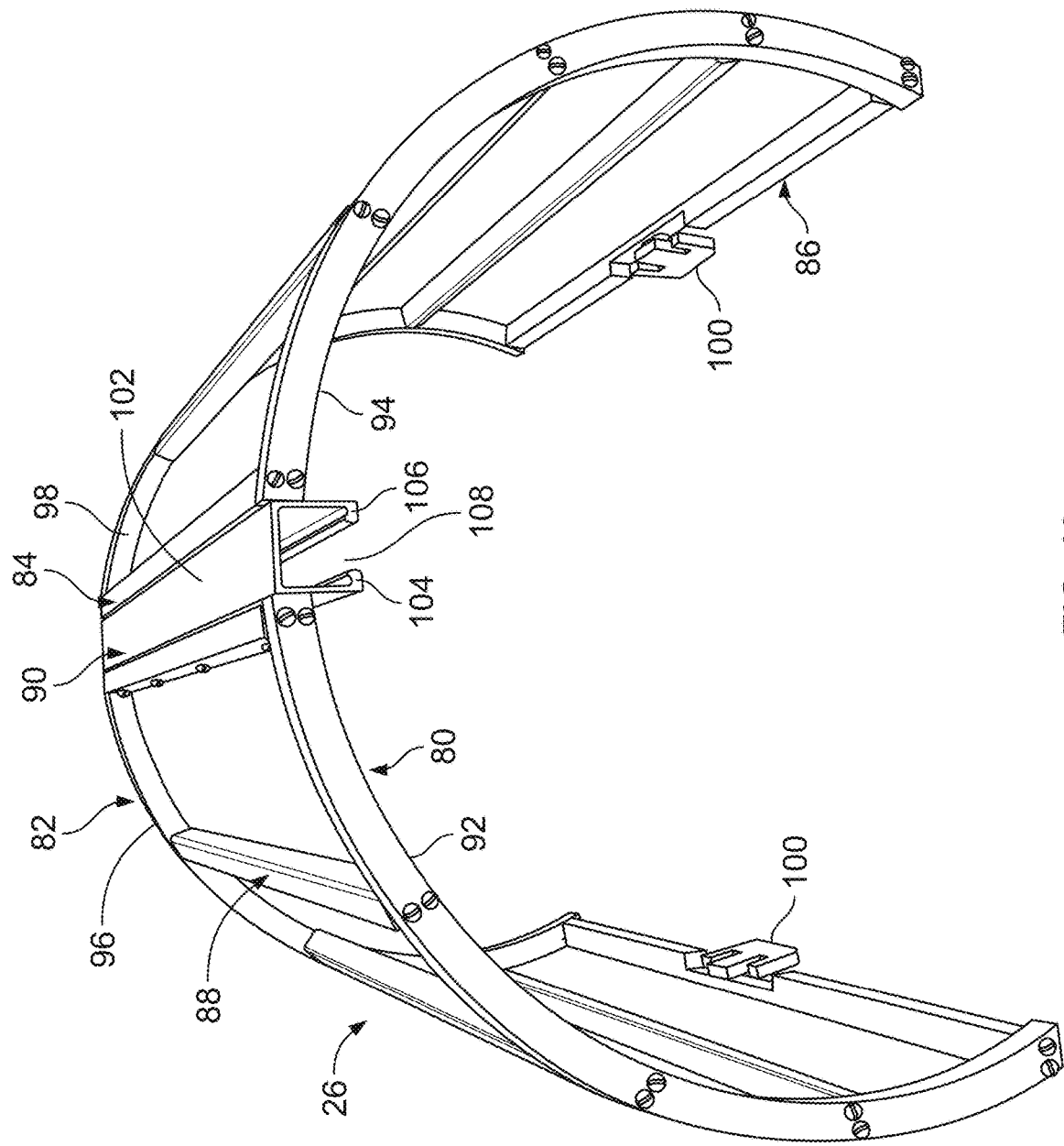

Referring now to FIGS. 12 and 13, support 26 is shown. As typical MRI machines are expensive and produced without means for supporting tablet 22, the present disclosure provides a retrofit support 26 to eliminate the need to modify standard MRI machines 12. While support 26 is described herein as being mounted within bore 16 of an unmodified MRI machine 12, it should be understood that support 26 may be integral to MRI machine 12 in other embodiments without departing from the teachings of the present disclosure. Support 26 of the present disclosure is formed to fit within bore 16 and thus provides a semi-circular support structure that conforms to the interior of MRI machine 12 and couples to the existing structure.

As shown in FIGS. 12 and 13, support 26 generally includes a curved brace 80, a curved brace 82, a pair of channel braces 84, a pair of lower braces 86 and a plurality of cross braces 88 extending between curved braces 80, 82. Support 26 further includes a channel 90 connected between channel braces 84. As best shown in FIG. 13, curved brace 80 includes a first section 92 and a second section 94, each extending between a lower brace 86 and a channel brace 84. Similarly, curved brace 82 includes a first section 96 and a second section 98, each extending between a lower brace 86 and a channel brace 84. A tab 100 is connected to each lower brace 86 and configured to mate with a connector within bore 16 of MRI machine 12 to fix support 26 in place. In one example, one or more hook-and-loop fasteners can be used for attachment purposes. Channel 90 includes an upper wall 102 and a pair of side walls 104, 106, which together form a C-shaped opening 108 sized to slidably receive a portion of mounting bracket 24 as is further described below.

Figure 14:
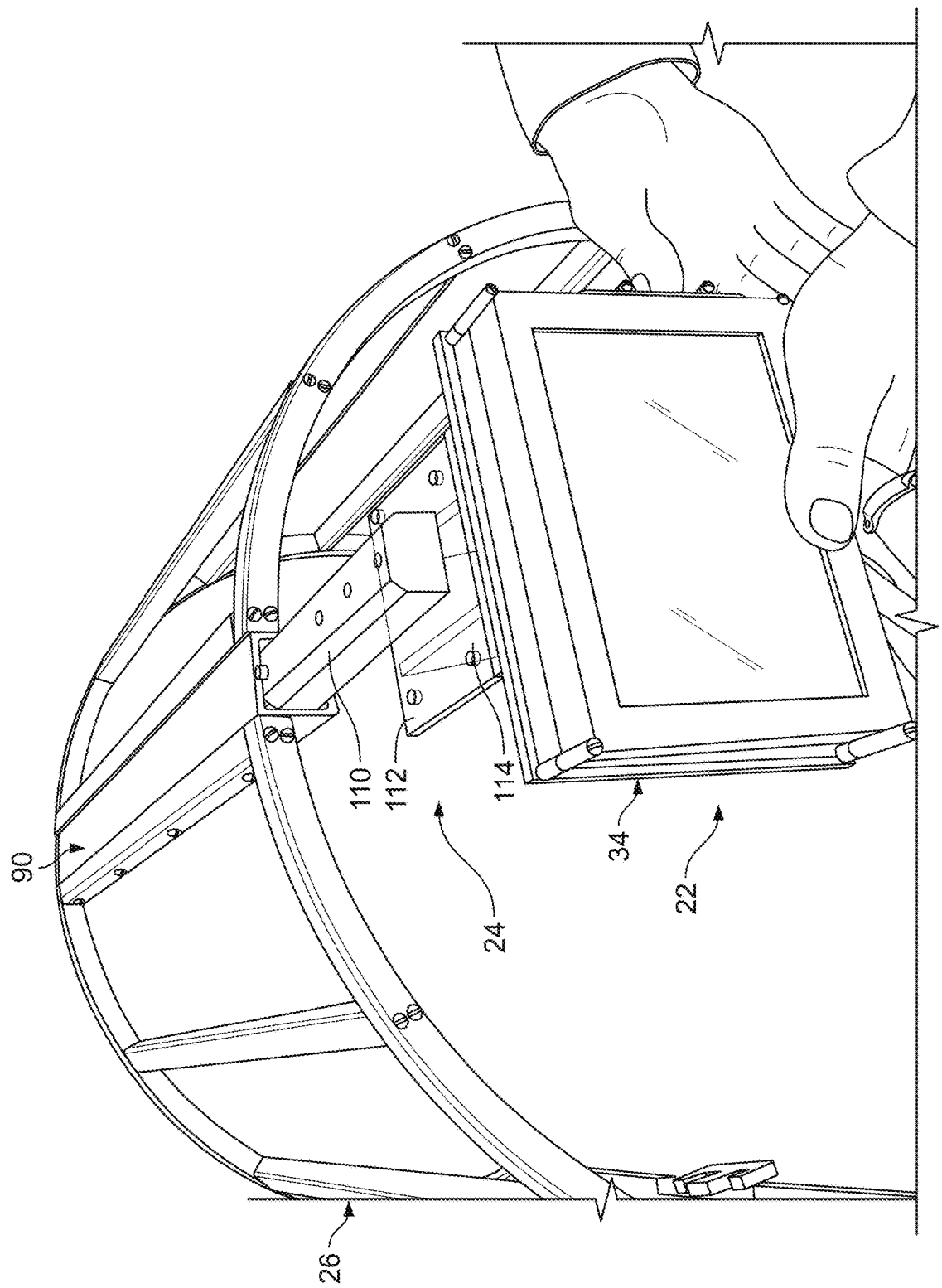
FIGS. 14-16 are perspective views depicting attachment of the tablet of FIG. 2 to the support of FIGS. 12 and 13.
Figure 15:
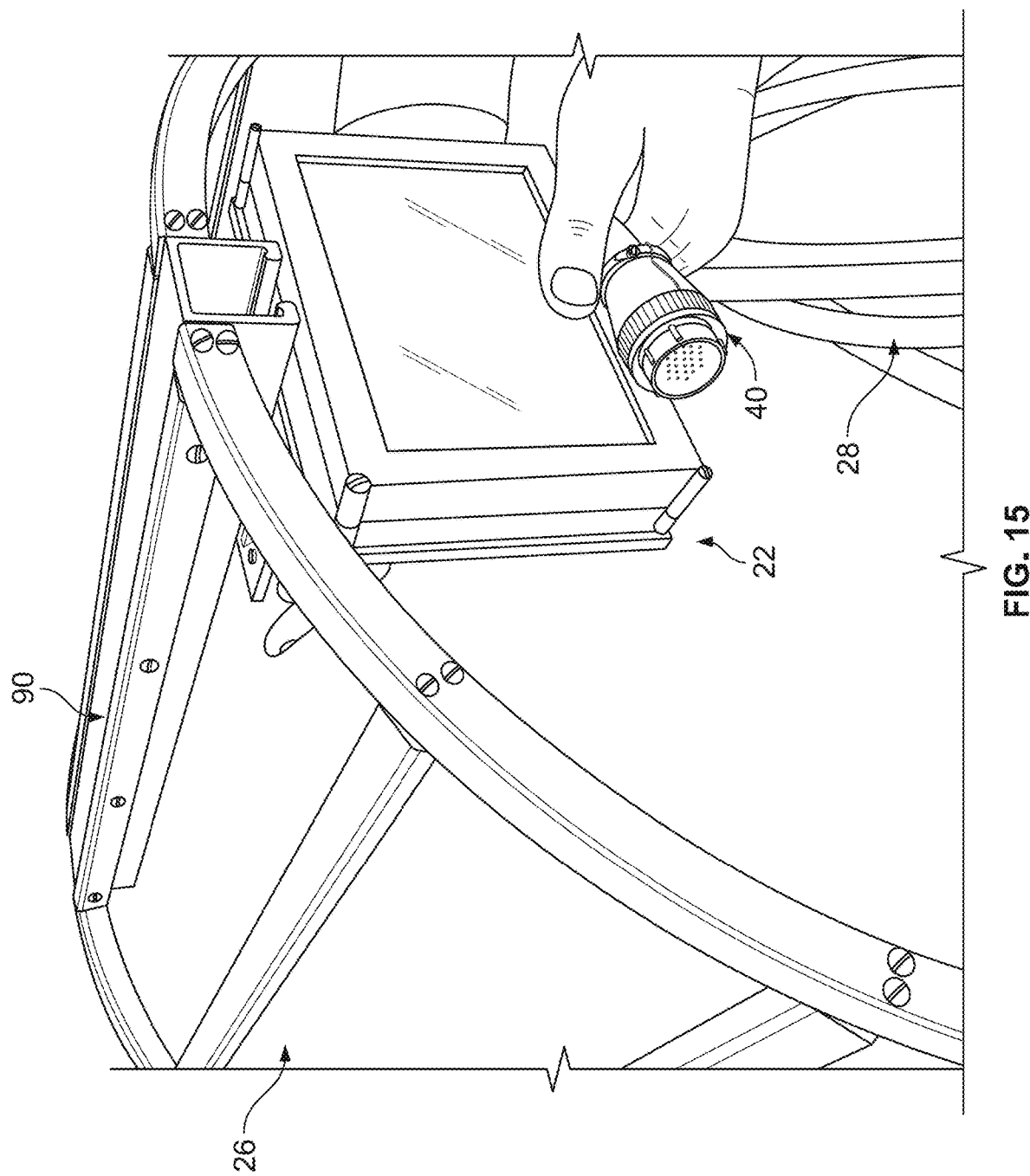
Figure 16:
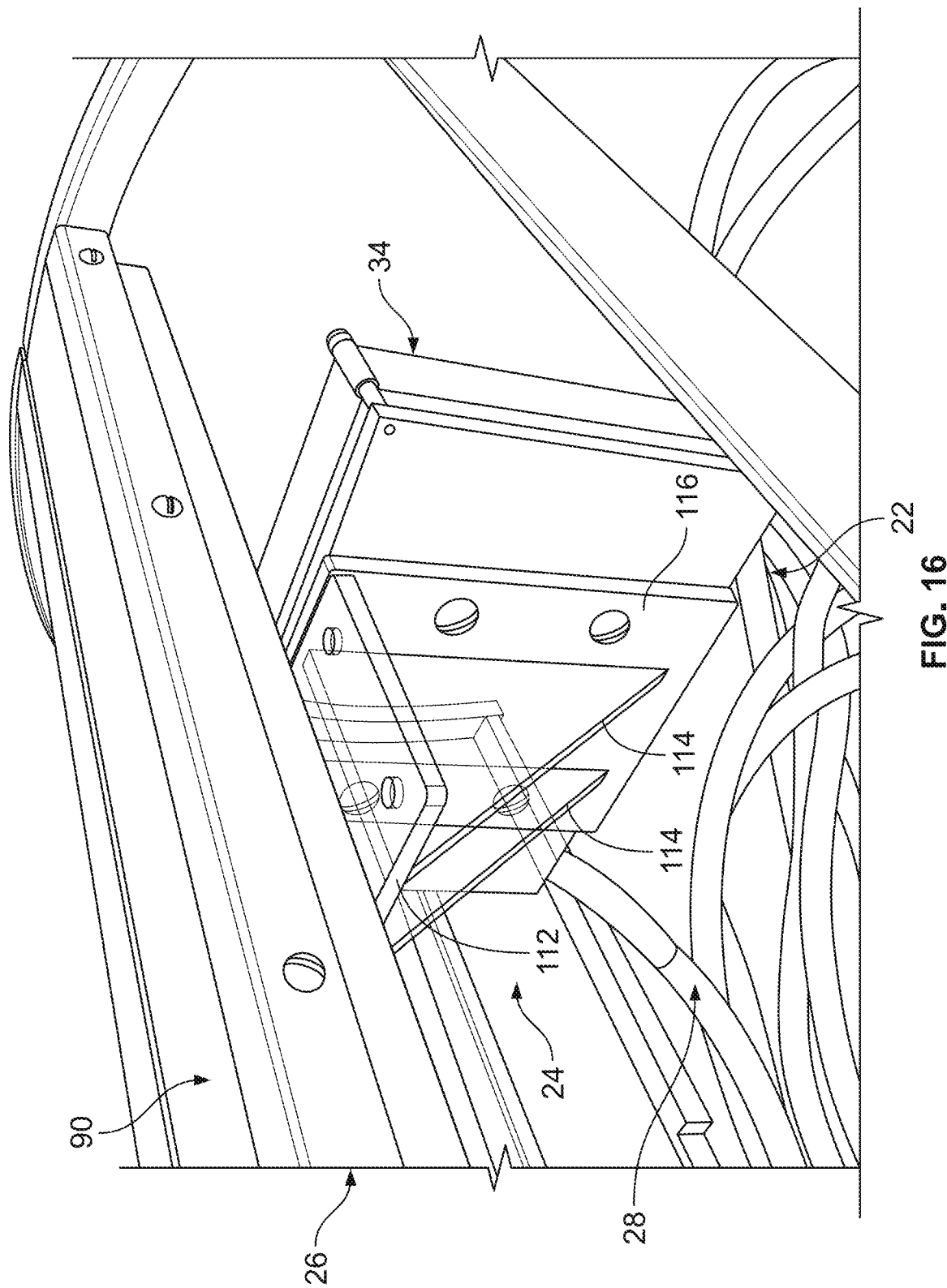

Referring now to FIGS. 14-16, mounting bracket 24 includes an insert 110 mounted to a top plate 112. Top plate 112 is connected to braces 114. As best shown in FIG. 16, a mounting plate 116 attached to housing 34 of tablet 22 is connected to top plate 112 and braces 114. As best shown in FIG. 14, insert 110 is sized to be received in opening 108 of channel 90. The sliding interface between insert 110 and opening 108 permits tablet 22 to be positioned at any location along the length of channel 90. While a particular embodiment of mounting bracket 24 is described, it should be understood that mounting bracket 24 may have a variety of acceptable configurations. The function of slidably connecting tablet 22 to channel 90 for adjustable positioning of tablet 22 may be carried out in many ways. Additionally, mounting bracket 24 may be configured in certain embodiments to permit tablet 22 to tilt, swivel, or otherwise assume various orientations.

Figure 17:
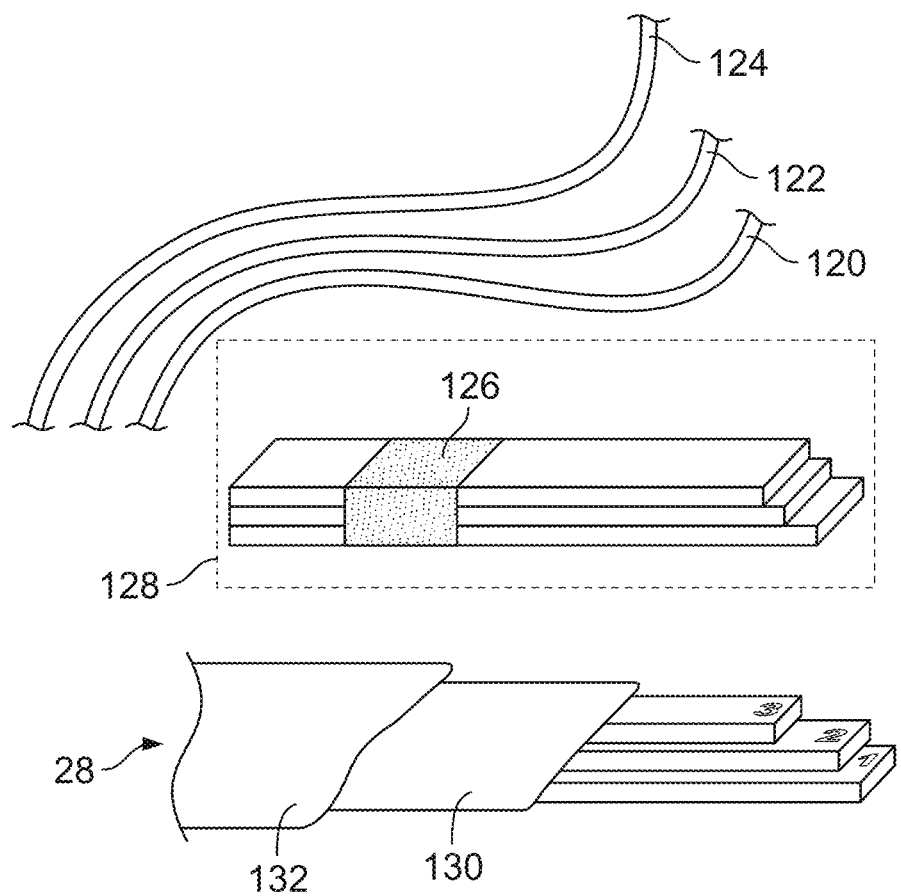
FIGS. 17-19 are perspective views of a cable of the tablet assembly of FIG. 2 at various stages of construction.
Figure 18:
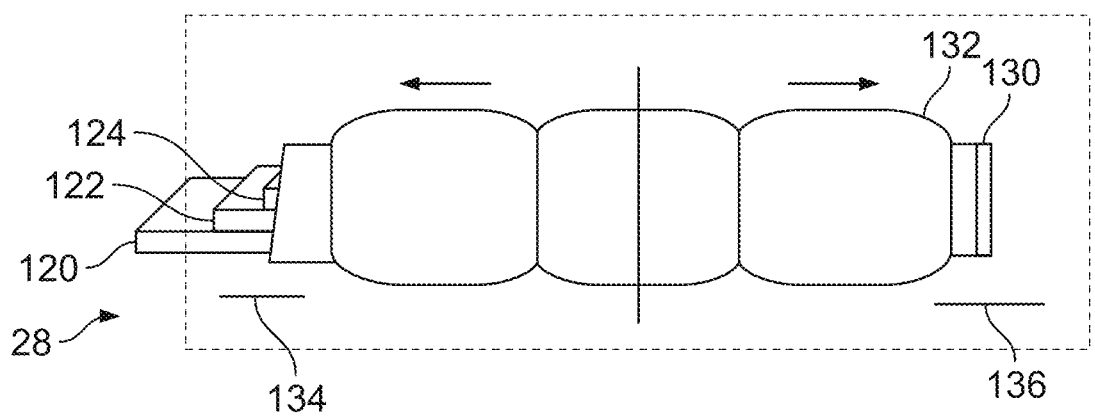
Figure 19:
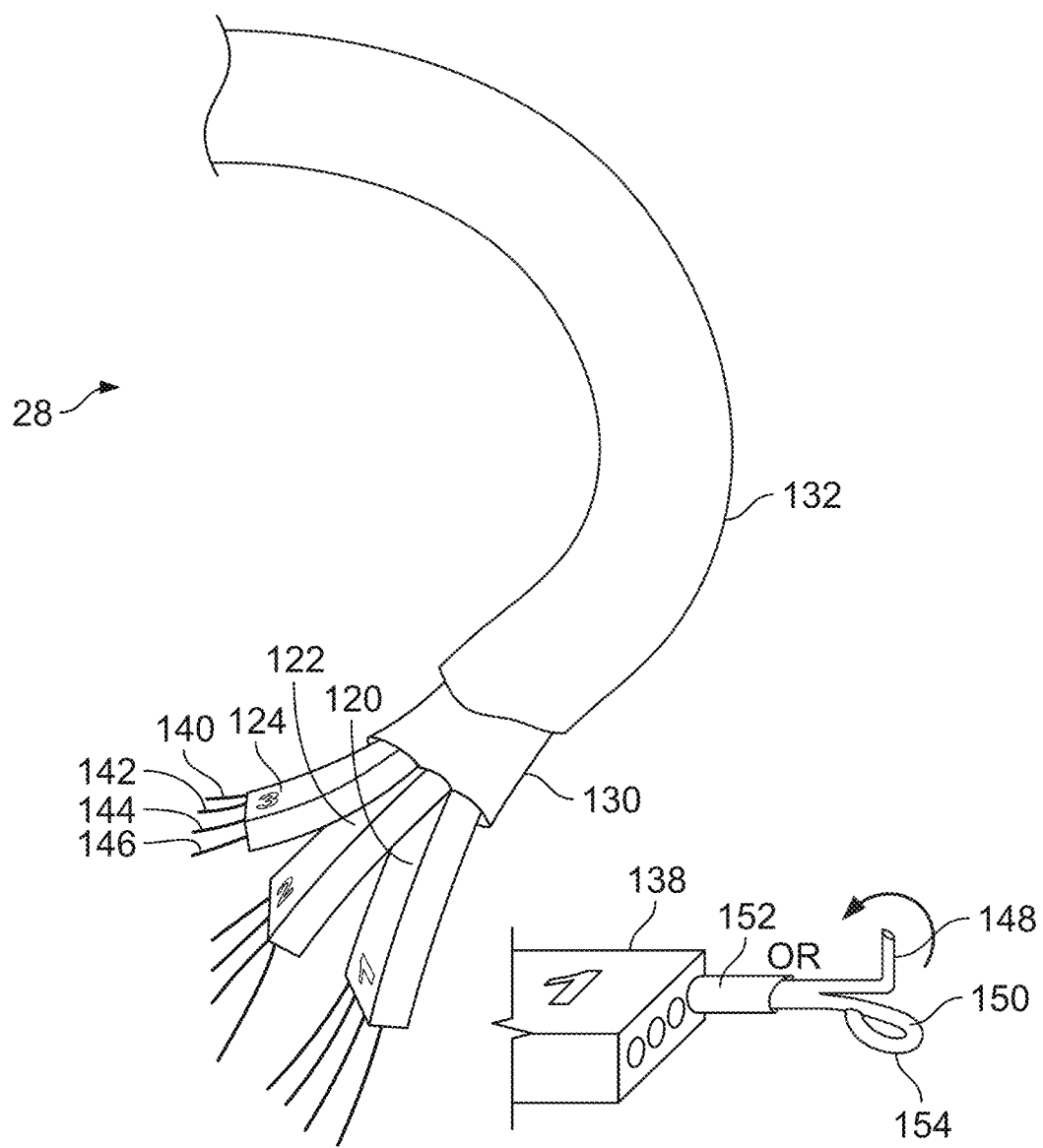
Figure 20:
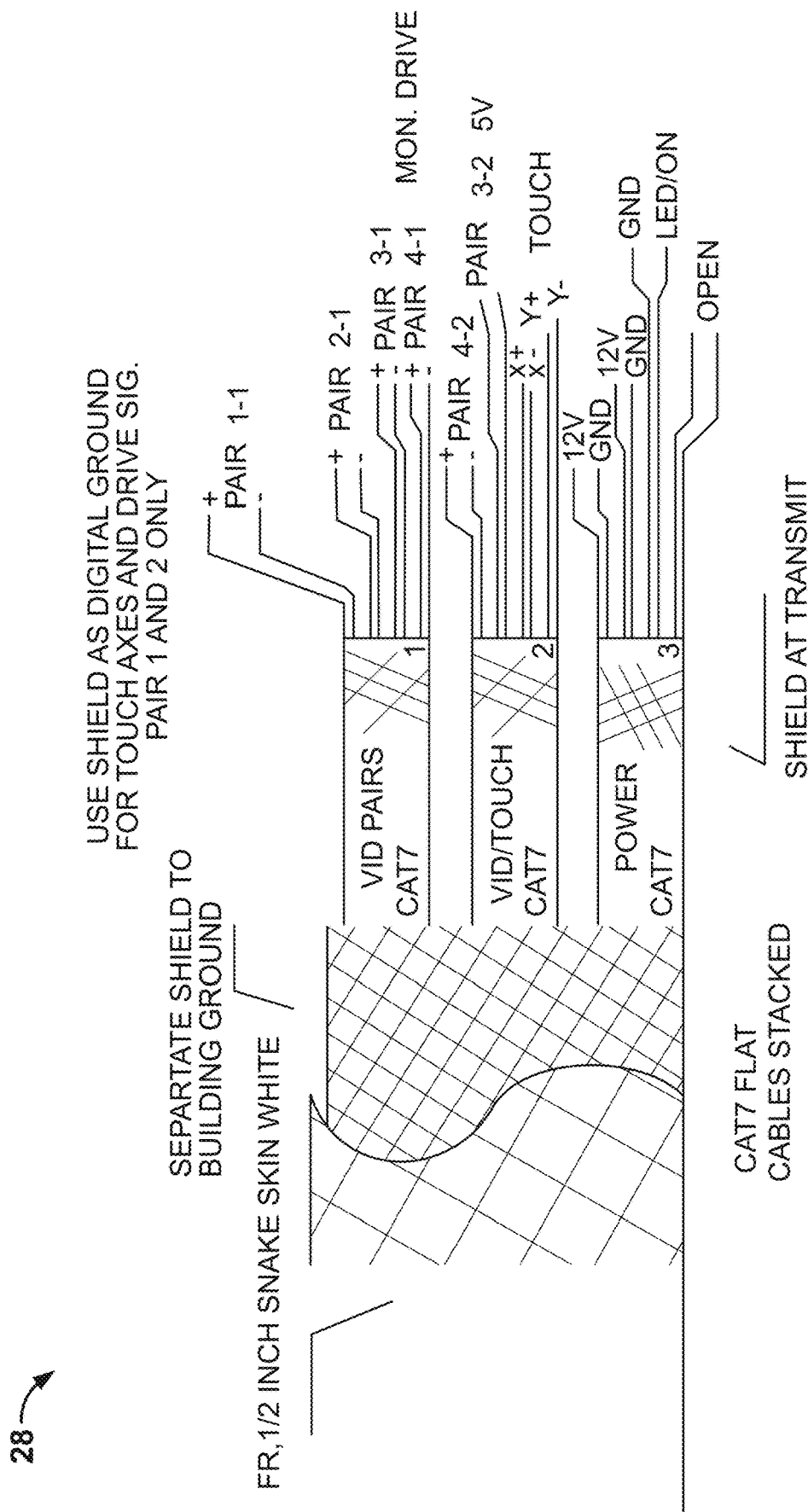
FIG. 20 is a schematic view of the cable of FIGS. 17-19.

Referring now to FIGS. 17-19, details of construction of one embodiment of cable 28 are shown. As best shown in FIG. 17, the electrically conductive component of cable 28 includes three identical Cat7 Ethernet cable sections 120, 122, 124. Sections 120, 122, 124 are stacked on one another and bound with tape 126, thereby forming a cable assembly 128. Cable assembly 128 is then pushed through a section of copper shielding braid 130 and an outer nylon jacket braid 132. As shown in FIG. 18, the braids 130, 132 are pushed back at ends 134, 136 of cable 28 after assembly is complete to expose the ends of cable sections 120, 122, 124. The ends of cable sections 120, 122, 124 are then stripped and connected to receiver board 48 and connector 40 in the manner described below. When the jacket 138 of each cable section 120, 122, 124 is removed as shown in FIG. 19, four wires 140, 142, 144, 146, each having two conductors 148, 150, are exposed. The insulation 152 of each wire 140, 142, 144, 146 is stripped to expose conductors 148, 150. Conductors 148, 150 are then folded back upon themselves and solder 154 is applied to prepare conductors 148, 150 for connection to receiver board 48 and connector 40. A wiring diagram of cable 28 is depicted in FIG. 20.

Figure 21:
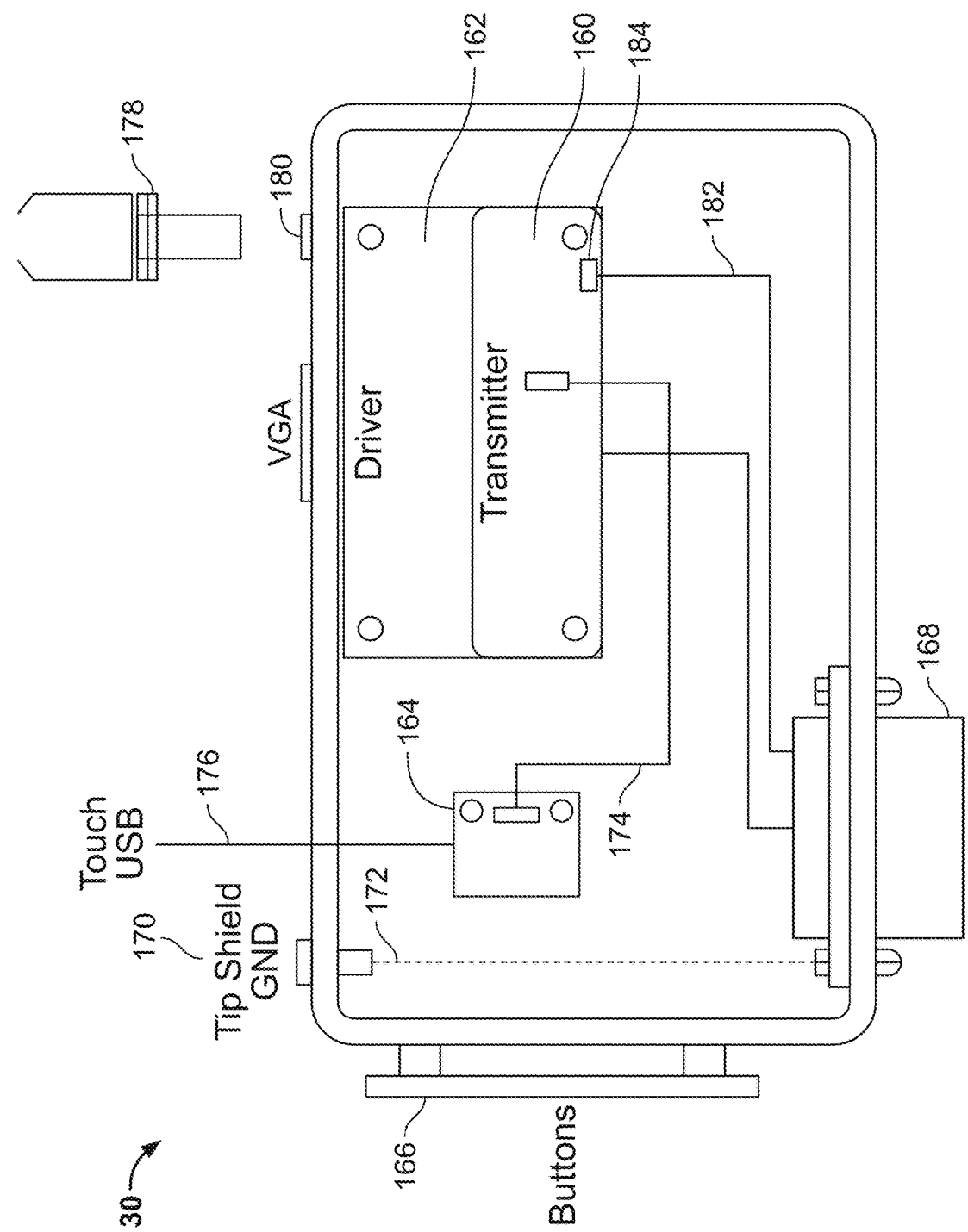
FIG. 21 is a top, plan view of an interface box of the tablet assembly of FIG. 2.

Referring now to FIG. 21, interface box 30 is depicted. As shown, box 30, which may be an ABS plastic box, generally includes a transmitter board 160, a driver board 162, a touchscreen driver board 164 (such as the STMPE610), a button board 166 and a female magnesium 24 pin connector 168. A tip jack 170 is also connected to box 30. A shielded ground wire 172 is soldered to tip jack 170. As interface box 30 is normally powered by an isolated wall power supply, to effectively shield box 30 and MRI machine 12 from external signals, all grounding and RF shielding should be routed to building ground and is connected either through the AC outlet ground or the MRI pass panel via tip jack 170. A female Molex four pin jumper cable 174 is connected to transmitter board 160 and touchscreen driver board 164 as further described herein. A mini US connector 176 is connected to touchscreen driver board 164. A 12 V DC power supply plug 178 is attached to a power jack 180 mounted to box 30 and connected to driver board 162. Finally, a female Molex five pin power connector 182 is connected between connector 168 and a power connector 184 mounted to transmitter board 160 as is further described herein.

Figure 22:
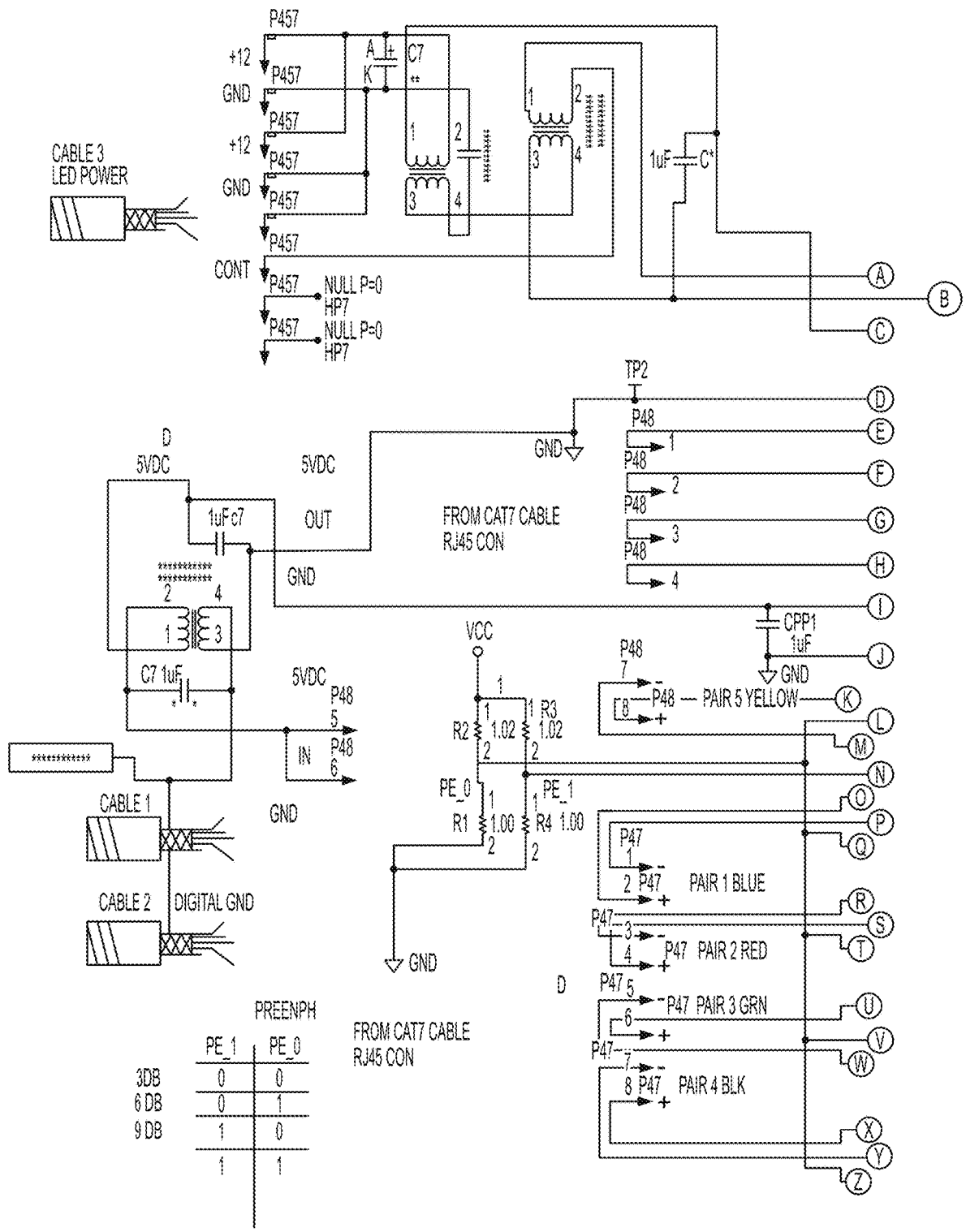
FIG. 22 is a schematic view of a receiver board of a tablet according to the present disclosure.
Figure 22:
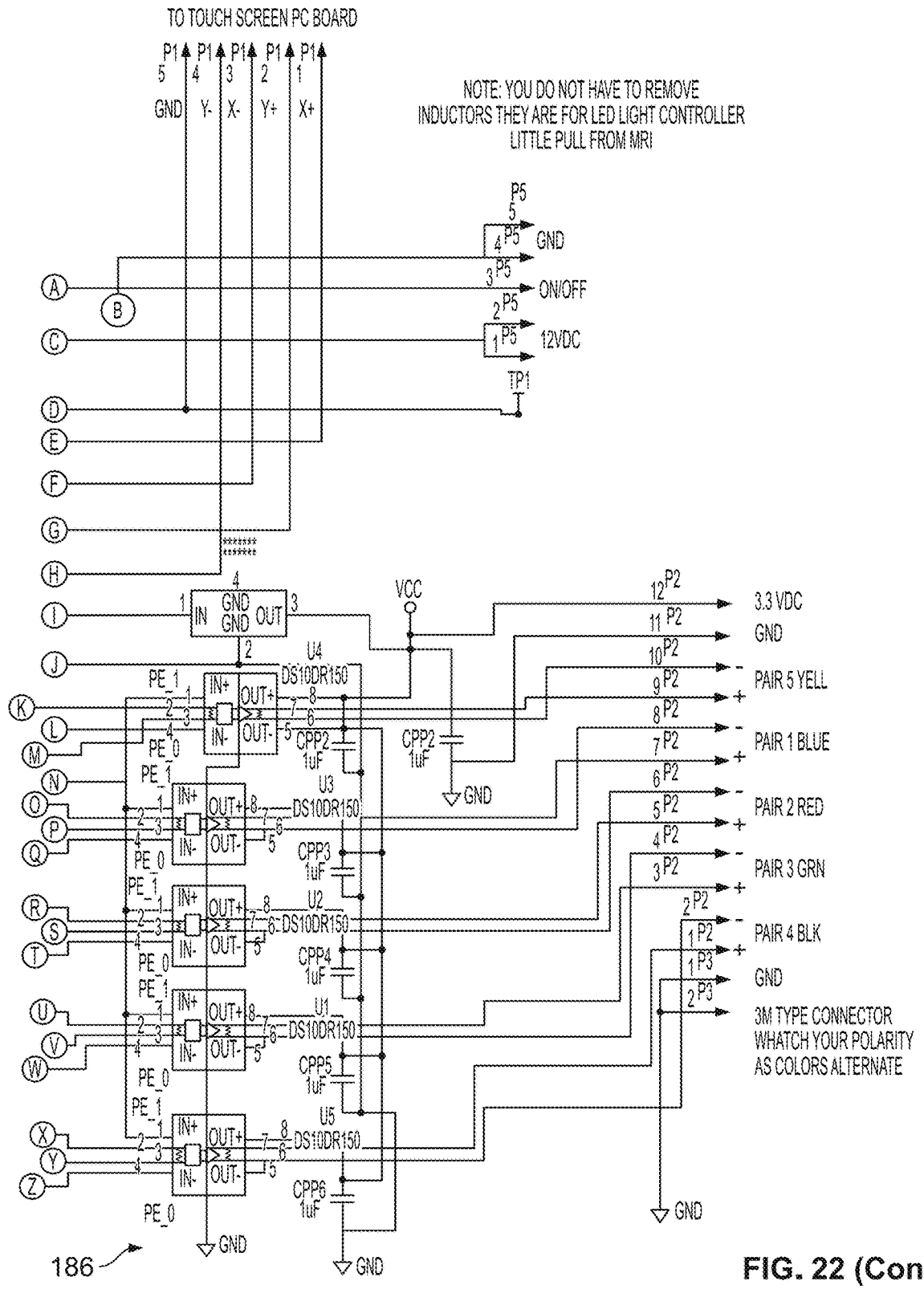
Figure 23:
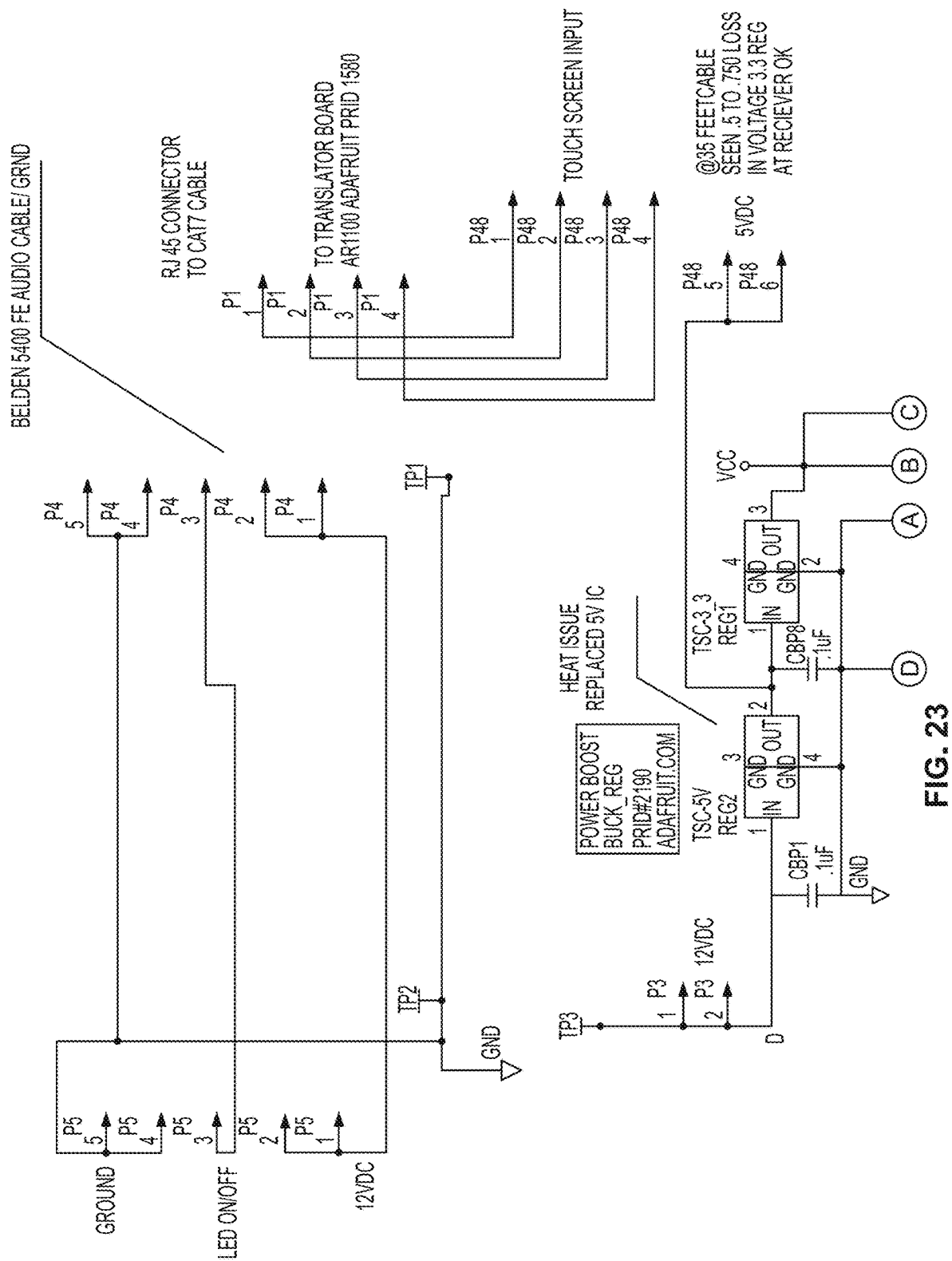
FIG. 23 is a schematic view of a driver board of the interface box of FIG. 21.
Figure 23:
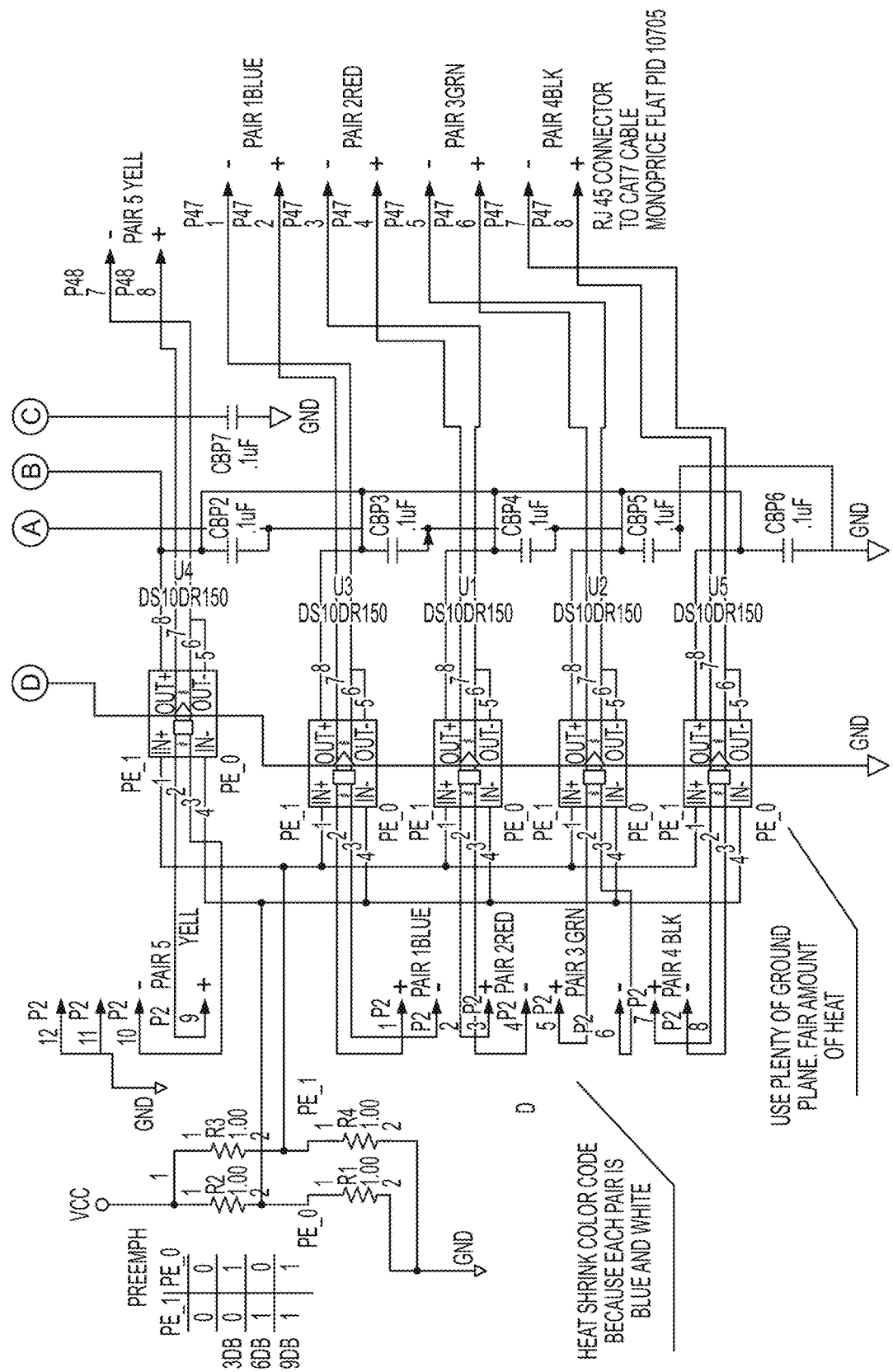
Figure 24:
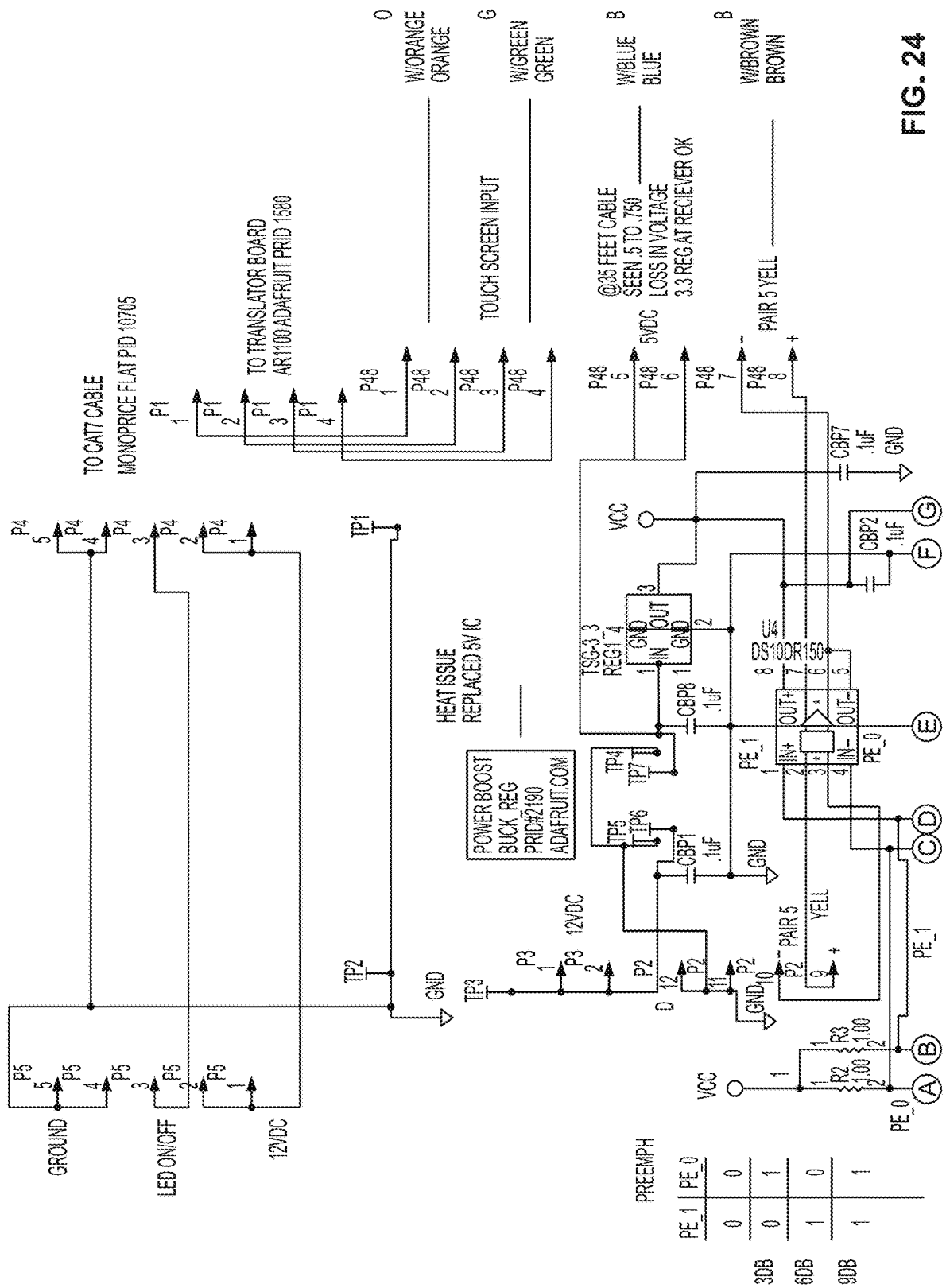
FIG. 24 is a schematic view of a transmitter board of the interface box of FIG. 21.
Figure 24:
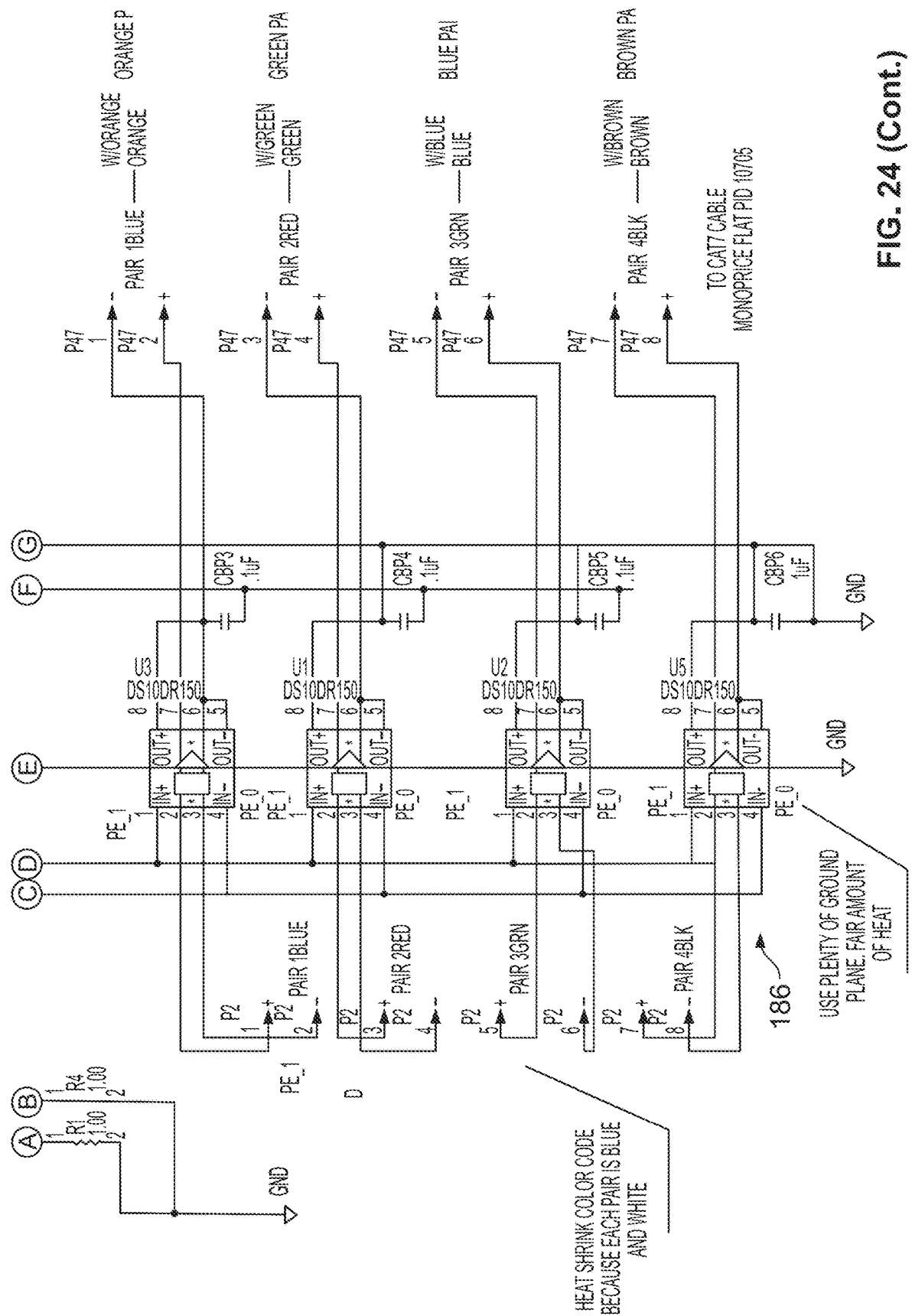
Figure 25:
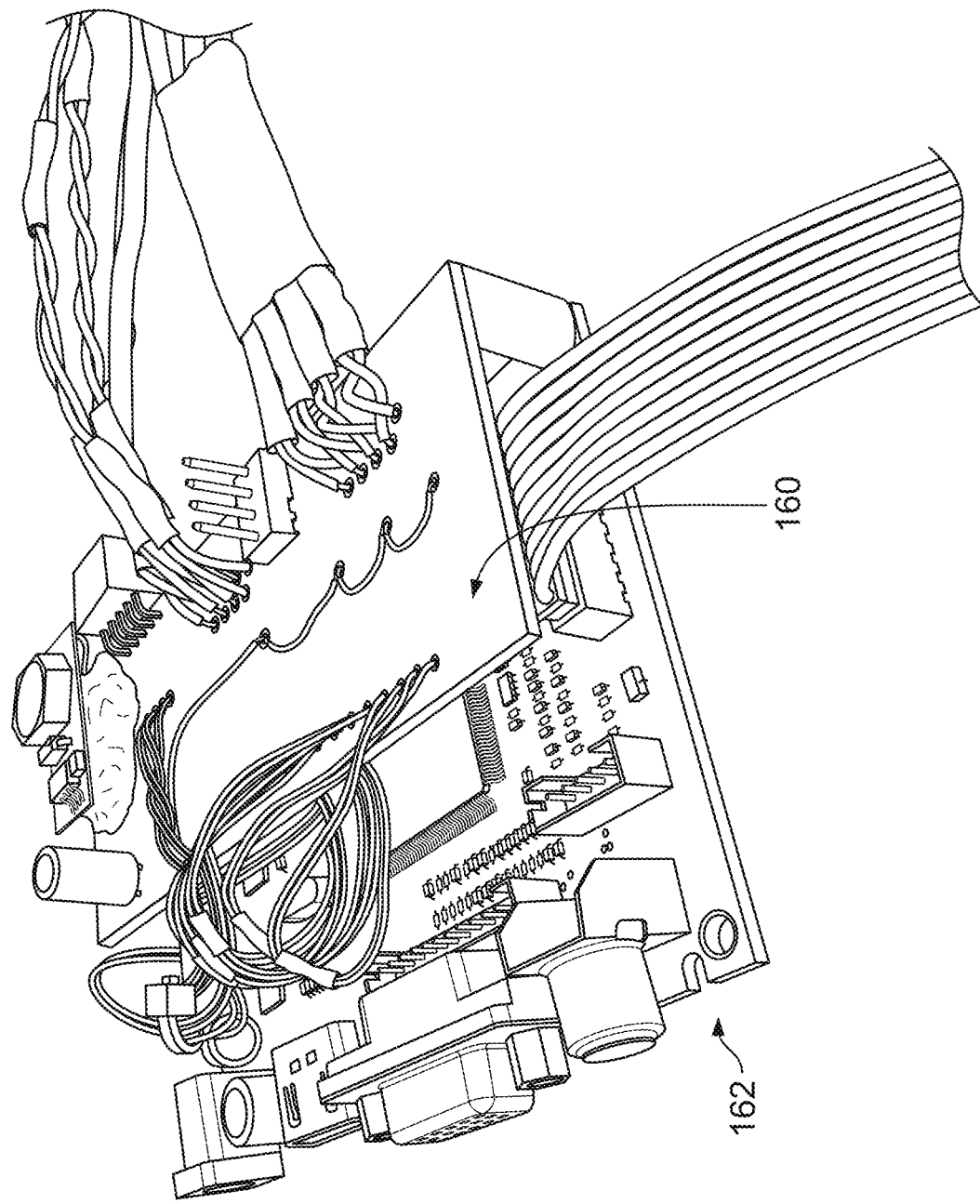
FIG. 25 is a perspective view of an assembly including the driver board of FIG. 23 and the transmitter board of FIG. 24.
Figure 35:
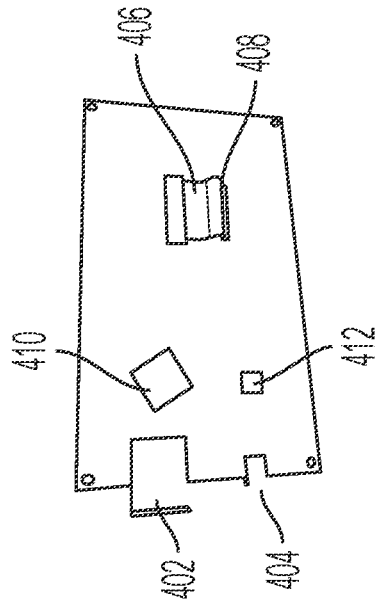
FIGS. 34-37 are perspective views of a display control board according to the present disclosure.
Figure 37:
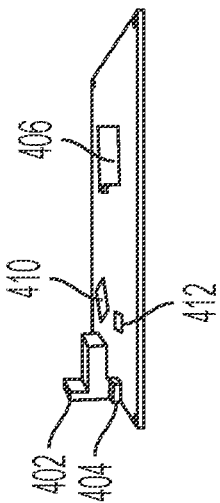

FIG. 22 is a schematic diagram of receiver board 48 mounted within housing 34 of tablet 22. As shown, receiver board 48 uses a plurality of buffers 186 such as the DS10BR150 1.0 Gbps LVDS Buffer/Repeater available from Texas Instruments. FIG. 23 is a schematic diagram of driver board 162 (FIG. 21) of interface box 30. FIG. 24 is a schematic diagram of transmitter board 160 (FIG. 21) of interface box 30. As shown, transmitter board 160 also uses a plurality of buffers 186. Finally, FIG. 25 is a photograph depicting driver board 162 and transmitter board 160.

Referring now to FIGS. 26-29, another embodiment of a table housing 200 used with tablet 22 is conceptually depicted as including a front housing assembly 202 and a rear housing assembly 204. In embodiments, table housing 200 includes MR-compatible electronics having at least one layer of carbon fiber on an outer surface of table housing 200 such that components in table housing 200 are protected from external signals. Also, the carbon fiber layer prevents any internal electrical signals from interfering with the MRI images received from MRI machine 12. An exemplary resolution for touchscreen display 36 is 800×450 pixels. Exemplary dimensions of table housing 200 are 105×175× 60 millimeters. In one embodiment, each carbon layer is assembled as a plastic 3D-printed frame coated with an aerosol applied carbon film. In one embodiment, each carbon layer is connected by a copper wire to each of the other frames. As such, the carbon layer(s) provide a shielded environment for the components disposed in tablet housing 200.

As shown in FIG. 26, front housing assembly 202 includes a top panel 206, a bottom panel 208, a first side panel 210, a second side panel 212, and a front panel 214. Each panel 206-214 has a substantially quadrilateral shape and an outer periphery of each panel includes at least partially a beveled face 216 at about 45 degrees such that connecting seams created by adjacent panels (e.g., panels 206 and 212) are closely abutted when assembled. An opening 218 (e.g., 133×105 mm) is provided in front panel 214 for viewing touchscreen display 36. An exemplary width of top panel 206 is about 133 millimeters. An exemplary length of side panels 210, 212 is about 77 millimeters, and an exemplary width of side panels 210, 212 is about 12 millimeters. Each panel 206-214 can be a carbon fiber board having an exemplary thickness of about 2 millimeters to provide enhanced structural strength and integrity while reducing an overall weight. For example, a weave construction of the fiber provides a resistive reactance of the signals, and any eddy currents generated by MRI machine 12 dissipate within the fiber. In one embodiment, panels 206-214 can be assembled with a conductive epoxy but can also be molded with a carbon fiber fabric.

As shown in FIG. 28, rear housing assembly 204 includes a top panel 222, a bottom panel 224, a first side panel 226, a second side panel 228, and a rear panel 230. As with front housing assembly 202, each panel 222-230 has a substantially quadrilateral shape and an outer periphery of each panel includes at least partially beveled face 216 at about 45 degrees. In first side panel 226, a first opening 232 is provided for installing a power on/off switch 236, and a second opening 234 is provided for installing a charge cover 238. An exemplary height of switch 236 is about 10 millimeters and an exemplary outer diameter of switch 236 is about 12 millimeters. An exemplary length of charge cover 238 is about 30 millimeters and an exemplary width of charge cover 238 is about 12 millimeters. A cable connector 220 is also provided in at least one of bottom panel 208 of front housing assembly 202 and bottom panel 224 of rear housing assembly 204. In one embodiment, cable connect 220 is installed about 33 millimeters from a longitudinal outer edge of corresponding bottom panel 208, 224.

Figure 34:
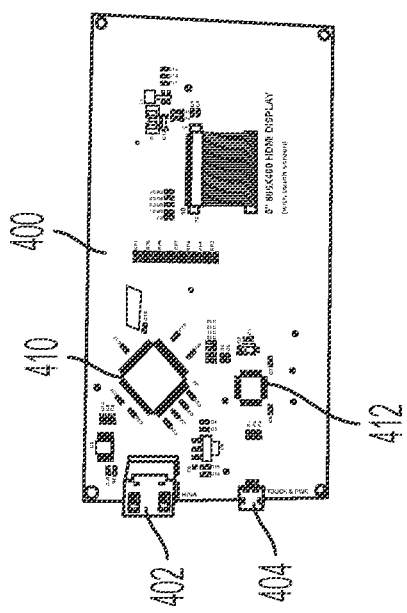
Figure 36:
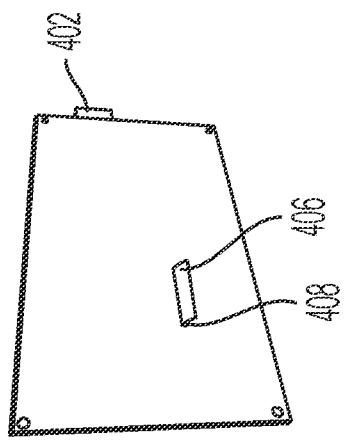
Figure 40:
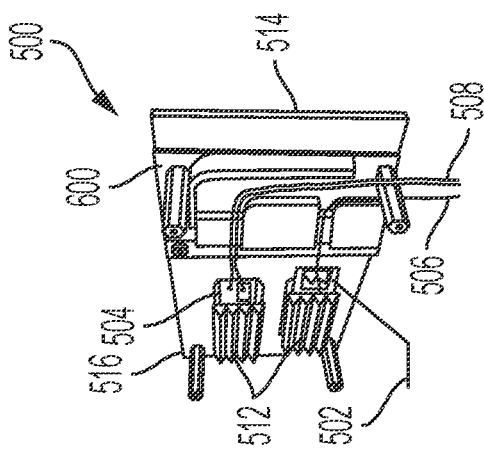
FIGS. 38-43 are perspective views of an optical drive board according to the present disclosure.
Figure 43:
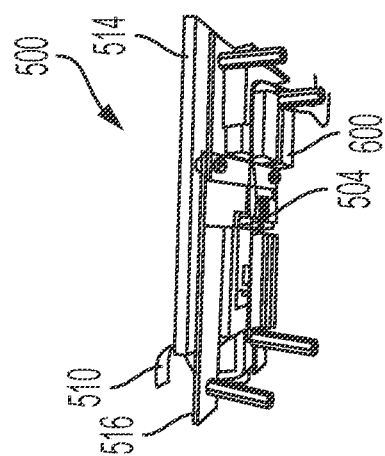
Figure 39:
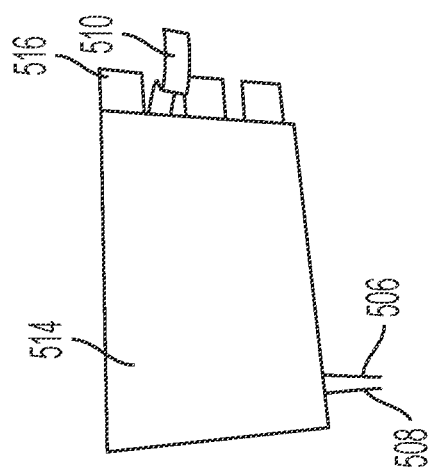

Referring now to FIGS. 30-33, a display housing assembly 300 of tablet 22 is shown as including a front housing support 302, a LCD monitor 304, and a rear housing support 306. In one embodiment, LCD monitor 304 can be a liquid crystal display monitor. In embodiments, front housing support 302 includes an opening 308 for viewing images displayed on LCD monitor 304. An exemplary dimension of opening 308 is about 118×74 millimeters. Also, rear housing support 306 includes an opening 310 for providing access to cables connected to LCD monitor 304 and other relevant components, such as a display control board 400 (FIG. 34). An exemplary dimension of opening 310 is about 76×38 millimeters.

Further, as shown in FIGS. 31 and 33, a strip 312 made of copper, carbon, nickel, or any combination thereof can be applied at least partially along outer edges of front housing support 302 and/or rear housing support 306. In one embodiment, front housing support 302 includes a shielded window 314 having a fine copper mesh. As such, conductive layers, such as the fine copper mesh, provides a shielded environment. In other embodiments, an RF resistant glass with a copper coating on the inside of front housing support 302 may be used as shielded window 314. Front and rear housing supports 302, 306 can be attached together to provide structural support for LCD monitor 304. For example, front and rear housing supports 302, 306 can be glued together using adhesives. As shown in FIG. 31, LCD monitor 304 is sandwiched between front and rear housing supports 302, 306.

Figure 38:
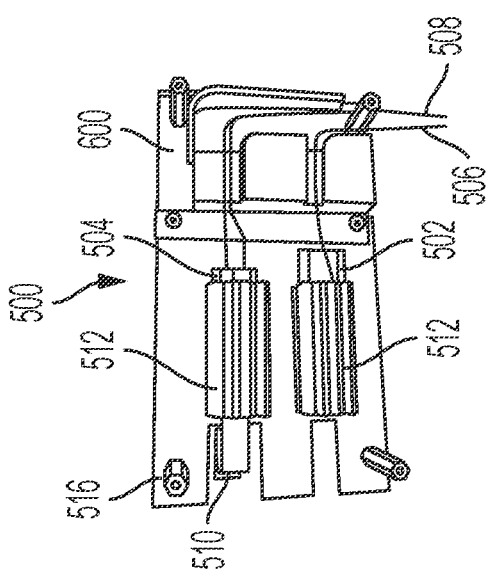
Figure 41:
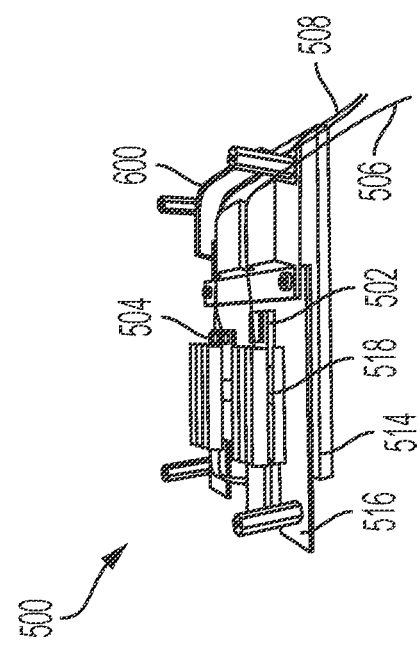
Figure 45:
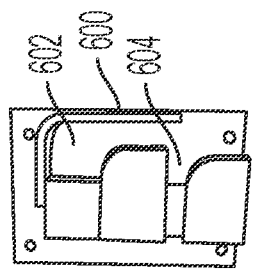
FIG. 45 is a front view of the cable guide of FIG. 44.
Figure 47:
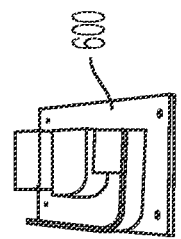
FIG. 47 is a perspective views of the cable guide of FIG. 44.
Figure 44:
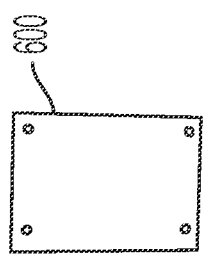
FIG. 44 is a rear view of a cable guide according to the present disclosure.
Figure 46:
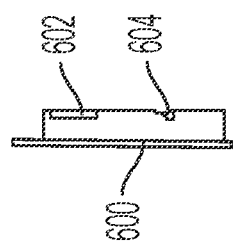
FIG. 46 is a side view of the cable guide of FIG. 44.
Figure 49:
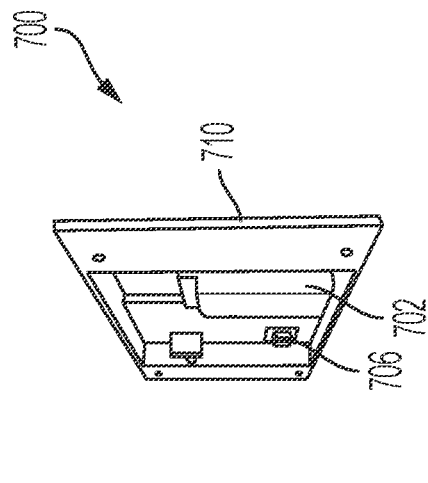
FIGS. 48-51 are perspective views of a power supply housing according to the present disclosure.
Figure 51:
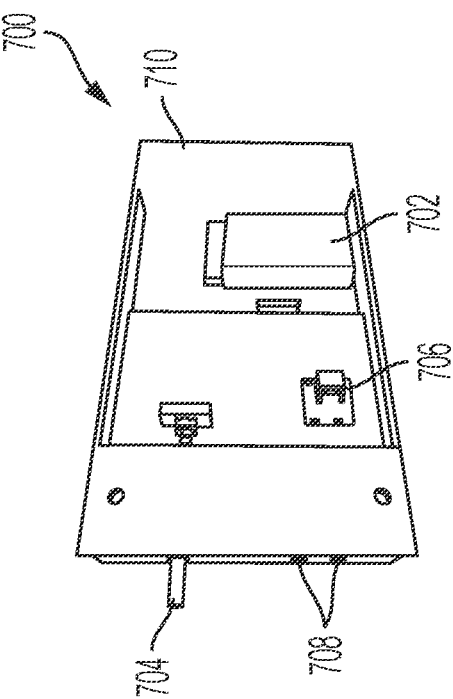

Referring now to FIGS. 34-37, a display control board 400 configured to control operations of LCD monitor 304 is shown. In embodiments, display control board 400 includes an HDMI port 402, a USB port 404, an LCD driver controller 410, and a USB touchscreen controller 412. For example, LCD driver controller 410 converts the HDMI signals to low voltage differential signals (LVDSs) to control LCD monitor 304 using a flat ribbon cable 406 operatively connected to LCD monitor 304. In one embodiment, USB touchscreen controller 412 can be connected to a USB host port fiber driver 502 of an optical driver assembly 500 (FIG. 38). An opening 408 is provided in display control board 400 for redirecting cable 406 as desired.

Figure 42:
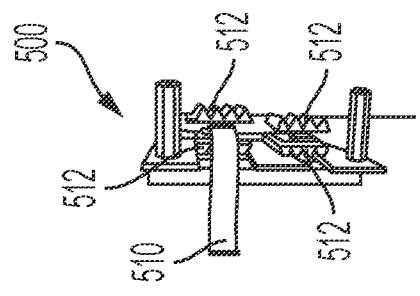

Referring now to FIGS. 38-43, optical driver assembly 500 is shown and configured to convert an optical signal received from interface box 30 via cable 28. Since an optical fiber interface is used, tablet 22 can be impervious to external or internal noise. In embodiments, optical driver assembly 500 includes USB host port fiber driver 502 connected to a USB optic cable 506, and a HDMI driver 504 connected to a HDMI optic cable 508. In the illustrated embodiment, cable 28 includes optic cables 506, 508. For example, the optical signal can be duplex multimodal to allow fast data speeds without interference or noise. In one embodiment, a flat ribbon cable 510 can be connected to HDMI driver 504 for facilitating communication with display control board 400. Also, as shown in FIG. 42, each driver 502, 504 is sandwiched between two separate heat sinks 512 to distribute the heat generated by the light source transmitted via optic cables 506, 508. For example, heat sinks 512 can be made of ceramic. In another embodiment, HDMI driver 504 can be adaptable to fiber optic cables in glass or plastic.

Figure 48:
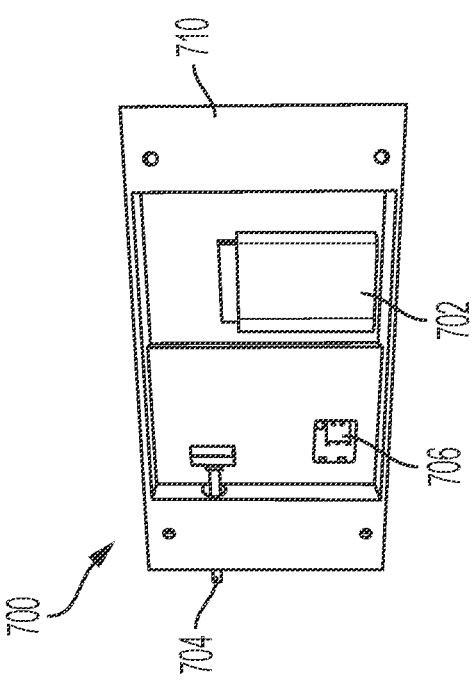
Figure 50:
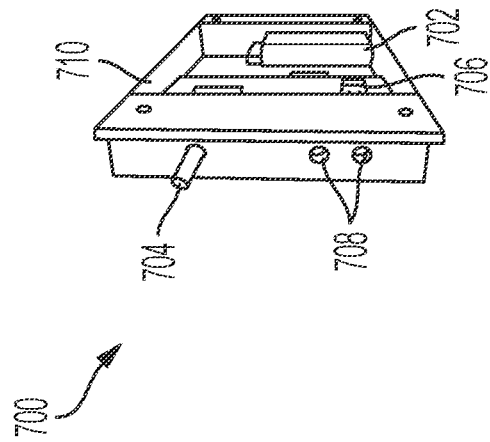
Figure 53:
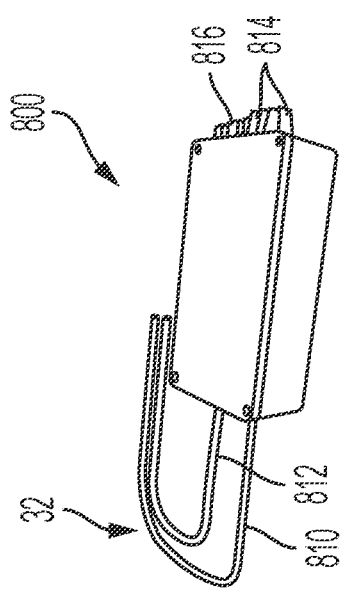
FIGS. 52-55 are perspective views of another interface box according to the present disclosure.
Figure 55:
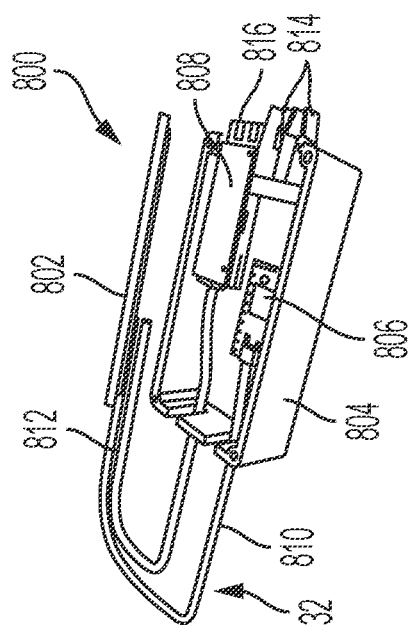
Figure 52:
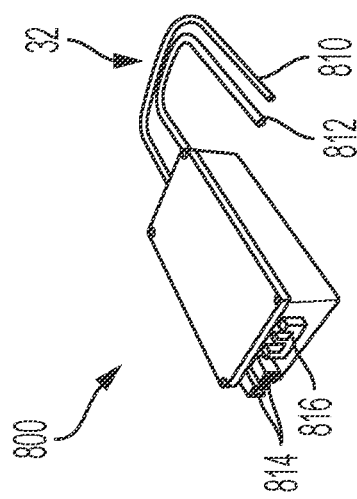
Figure 54:
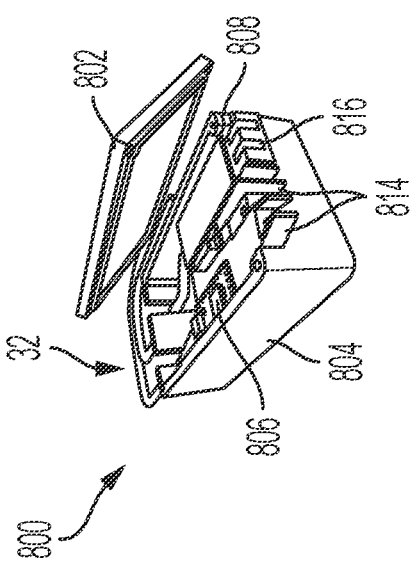
Figure 57:
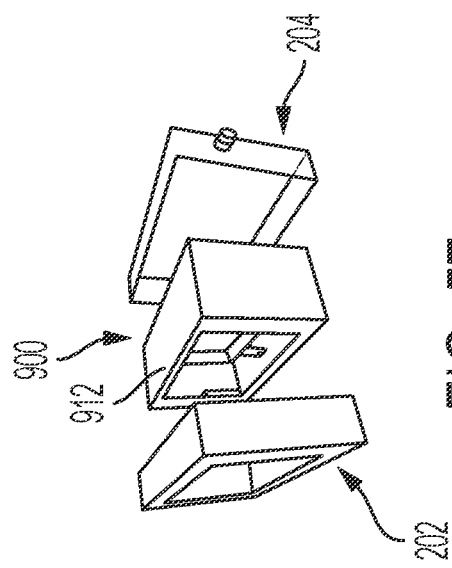
FIGS. 57-59 are exploded views of the shielding jacket of FIG. 56 used with the tablet housing shown in FIGS. 26-29 according to the present disclosure.
Figure 59:
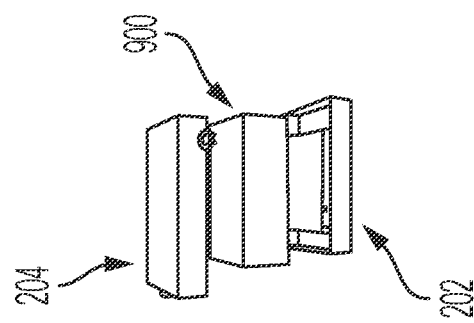
Figure 56:
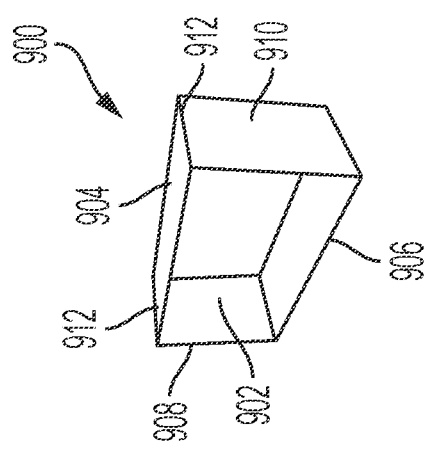
FIG. 56 is a perspective view of a shielding jacket according to the present disclosure.
Figure 58:
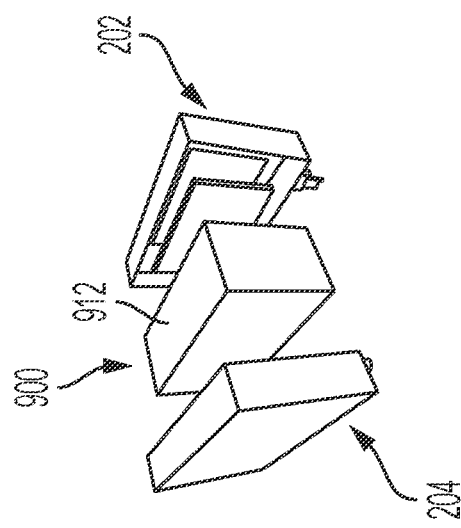

In the illustrated embodiment, both drivers 502, 504 are disposed on a base board 516 having a protective pad 514 (e.g., 132×85 mm). For example, protective pad 514 is a carbon felt pad disposed behind base board 516 to protect drivers 502, 504 from heat and noise. In one embodiment, a microcontroller 518 of USB host port fiber driver 502 can be connected to USB port 404 of display control board 400 for communication and power, and HDMI driver 504 can be similarly connected to HDMI port 402 of display control board 400 for communication and power via ribbon cable 510. In one embodiment, microcontroller 518 and/or USB host port fiber driver 502 can be self-powered, e.g., via USB port 404 or internal power source 702 (FIG. 48), without using an external power source or calibration software.

Referring now to FIGS. 44-47, optical driver assembly 500 includes a cable guide 600 for providing stability and support to drivers 502, 504 and optic cables 506, 508. In the illustrated embodiment, a first channel 602 is configured to receive HDMI optic cable 508, and a second channel 604 is configured to receive USB optic cable 506. Any suitable configurations, such as straight grooves, curved grooves, or combinations of both, are contemplated to suit different applications.

Referring now to FIGS. 48-51, a power supply assembly 700 is shown and configured to provide electric power to display control board 400. In the illustrated embodiment, power supply assembly 700 includes a power source 702, such as a battery, a power switch 704, and a power regulator 706. For example, power source 702 can include two 3.7-volt DC MRI-compatible batteries. In one embodiment, the batteries are self-regulating and have an internal capacitance that filters out most low- to medium-band noise. For example, the batteries can be attached to display control board 400. In another embodiment, power source 702 can be a 12-volt DC power source.

One or more power ports 708 are provided to receive power from an external source (not shown), and the received power is transmitted to power regulator 706. In one embodiment, power regulator 706 simultaneously charges power source 702 and delivers the power to power switch 704 connected to display control board 400. When the external source is not available, power source 702 can provide the power to display control board 400 using power switch 704. At least one of power source 702, power switch 704, and power regulator 706 can be attached to a support plate 710.

Referring now to FIGS. 52-55, another embodiment of interface box 30 is shown. In the illustrated embodiment, an interface box 800 includes a cover 802 and a base 804 having a USB optical drive 806 and a HDMI optical drive 808. In one embodiment, cover 802 is configured to protect base 804 from electromagnetic interference (EMI) noise and provide heat dissipation from internal components. For example, interface box 800 can be made of cast aluminum with a baked-on powder coat. Communication link 32 has a first cable 810 connected to USB optical drive 806, and a second cable 812 connected to HDMI optical drive 808. For example, both first and second cables 810, 812 are connected to corresponding ports of controller 20 to receive the signals sent out by controller 20. At least one USB port 814 is connected to USB optical drive 806, and similarly at least one HDMI port 816 is connected to HDMI optical drive 808. In embodiments, USB and HDMI ports 814, 816 are connected to tablet 22 via cable 28. For example, USB port 814 is connected to USB host port fiber driver 502 via USB optic cable 506, and HDMI port 816 is connected to HDMI driver 504 via HDMI optic cable 508.

Referring now to FIGS. 56-59, a shielding jacket 900 is provided to encase one or more components of tablet 22. For example, display housing assembly 300, display control board 400, optical driver assembly 500, and power supply assembly 700 can be inserted into a cavity 902 defined by an inner surface of shielding jacket 900. In one embodiment, shielding jacket 900 includes a top wall 904, a bottom wall 906, a first side wall 908, and a second side wall 910 to define cavity 902. In one embodiment, shielding jacket 900 is made of a multi-metallized fabric, such as COBAL-TEX™. For example, the fabric can be cut to fit and folded around the components 300, 400, 500, 700 of tablet 22. Any existing external seams 912 can be attached together with a polyimide tape. In use, the fabric provides an RF shielding capability in the range of about 100 millihertz with a magnetic attenuation quality that does not interfere with the images received from MRI machine 12.

Referring now to FIGS. 60-61, an exemplary configuration of tablet 22 is shown including table housing 200 having display housing assembly 300, display control board 400, optical driver assembly 500, and power supply assembly 700. In this configuration, tablet 22 is encased by table housing 200 such that inner components of tablet 22 are protected from EMI noise during the MRI scanning. When assembled, table housing 200 prevents any internal electrical signals from interfering with MRI images received from MRI machine 12, thereby reducing MR-safety and MR-compatibility problems.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. For example, tablet 22 may be modified in certain embodiments to include other common computer peripherals such as a mouse, keyboard, trackball, speakers, etc. Accordingly, the scope of the present invention is intended to embrace all such alternatives, modifications, and variations as fall within the scope of the claims, together with all equivalents thereof.

Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. A system for recording visually guided motor activity within a bore of a Magnetic Resonance Imaging (MRI) machine, comprising:
    a tablet configured for mounting within the bore of the MRI machine, the tablet comprising a housing having a first opening, a touchscreen display encased within the housing for access through the first opening, a first shielding layer disposed over the touchscreen display and spanning the first opening, a second shielding layer disposed between the first shielding layer and the touchscreen display and spanning the first opening, and a receiver board encased within the housing, the housing being formed of an encasement material that reduces RF interference with the touchscreen display and the receiver board;
    an interface box coupled to a controller configured to control operation of the touchscreen display, the interface box being located remotely from the bore and comprising a transmitter board for processing signals from the controller and transmitting processed signals to the receiver board of the tablet; and
    a cable connected between the tablet and the interface box, the cable comprising a plurality of conductors to carry signals between the receiver board and the transmitter board.

2. The system of claim 1, wherein the encasement material of the housing is FR-4 composite material with copper cladding on both sides.

3. The system of claim 1, wherein the housing includes a 3D printed bottom plate and a 3D printed top plate that includes the first opening.

4. The system of claim 1, wherein the first shielding layer is formed from silver plastic mylar material.

5. The system of claim 4, wherein the second shielding layer is formed from copper mesh material.

6. The system of claim 1, wherein the touchscreen display is a touch-sensitive LCD display.

7. The system of claim 1, wherein the housing comprises a back wall, a forward wall, a pair of side walls, an upper wall and a lower wall, the walls being electrically joined together on interior and exterior sides using soldered copper tape.

8. The system of claim 7, wherein the forward wall includes the first opening and one of the side walls includes a second opening for receiving the cable.

9. The system of claim 7, wherein the interior side of each wall is beveled at an intersection with an adjacent wall.

10. The system of claim 1, wherein the cable comprises a plurality of Ethernet cable sections.

11. The system of claim 1, wherein a shielding braid surrounding the conductors is formed from copper.

12. The system of claim 1, wherein the cable further comprises an outer nylon jacket braid surrounding a shielding braid surrounding the conductors.

13. The system of claim 1, wherein the receiver board and the transmitter board each include a plurality of buffers.

14. A tablet assembly for recording visually guided motor activity within a bore of a Magnetic Resonance Imaging (MRI) machine, comprising:
a tablet configured for mounting within the bore of the MRI machine, the tablet comprising a housing having a first opening, a touchscreen display encased within the housing for access through the first opening, at least one shielding layer disposed over the touchscreen display and spanning the first opening, and a receiver board encased within the housing, the housing being formed of an encasement material that reduces RF interference with the touchscreen display and the receiver board;
an interface box located remotely from the bore and comprising a transmitter board for transmitting signals to the receiver board of the tablet; and
a cable connected between the tablet and the interface box, the cable comprising a plurality of conductors to carry signals between the receiver board and the transmitter board.

15. The tablet assembly of claim 14, wherein the encasement material of the housing is FR-4 composite material with copper cladding on both sides.

16. The tablet assembly of claim 14, wherein the at least one shielding layer comprises a silver plastic mylar layer and a copper mesh layer.

17. The tablet assembly of claim 14, wherein the cable comprises a plurality of Ethernet cable sections and a nylon jacket braid surrounding a shielding braid surrounding the conductors.

18. A tablet for a Magnetic Resonance Imaging (MRI) machine, the tablet comprising:
a housing including a front housing assembly having a first plurality of panels and a rear housing assembly having a second plurality of panels, the front housing assembly having a first opening, a touchscreen display encased within the housing for access through the first opening, at least one shielding layer disposed over the touchscreen display and spanning the first opening; and
at least one layer of carbon fiber formed on an outer surface of the housing as an encasement material that reduces RF interference with the touchscreen display, wherein the at least one layer of carbon fiber prevents an internal electrical signal from interfering with one or more MRI images received from the MRI machine.

19. The tablet of claim 18, wherein at least one panel of the first plurality of panels in the front housing assembly has a thickness of at least 2 millimeters, and at least one panel of the second plurality of panels in the rear housing assembly has a thickness of at least 2 millimeters.

20. The tablet of claim 19, wherein the at least one panel of the first plurality of panels in the front housing assembly and the at least one panel of the second plurality of panels in the rear housing assembly are assembled with a conductive epoxy.

21. The tablet of claim 19, wherein the at least one panel of the first plurality of panels in the front housing assembly and the at least one panel of the second plurality of panels in the rear housing assembly are molded with a carbon fiber fabric.

22. The tablet of claim 18, further comprising a display housing assembly including a front housing support, a monitor, and a rear housing support, wherein a strip made of at least one of: copper, carbon, and nickel is applied at least partially along an outer edge of at least one of: the front housing support and the rear housing support.

23. The tablet of claim 22, wherein the front housing support includes an opening for viewing one or more images displayed on the monitor, and the rear housing support includes an opening for providing access to at least one cable connected to the monitor.

24. The tablet of claim 22, wherein the front housing support includes a shielded window having a copper mesh.

25. The tablet of claim 18, further comprising an optical driver assembly configured to convert an optical signal received from an interface box coupled to a controller.

26. The tablet of claim 25, wherein the optical driver assembly includes a USB host port fiber driver connected to a USB optic cable, and a HDMI driver connected to a HDMI optic cable.

27. The tablet of claim 26, wherein each of the USB host port fiber drivers and the HDMI driver are sandwiched between two separate heat sinks.

28. The tablet of claim 18, further comprising an interface box including a cover and a base having a USB optical drive and a HDMI optical drive.

29. The tablet of claim 28, wherein the cover and the base are made of aluminum.

30. The tablet of claim 28, wherein the base includes at least one USB port connected to the USB optical drive, and at least one HDMI port connected to the HDMI optical drive.

31. The tablet of claim 18, further comprising a shielding jacket configured to encase at least one component of the tablet, wherein the shielding jacket is made of a multi-metallized fabric.

32. The tablet of claim 31, wherein one or more external seams associated with the shielding jacket are attached together with a polyimide tape.

* * * * *